United States Patent [19]

Urakami et al.

[11] Patent Number: 5,429,940
[45] Date of Patent: Jul. 4, 1995

[54] PROCESS FOR PRODUCING OXAZOPYRROLOQUINOLINES, NOVEL OXAZOPYRROLOQUINOLINES, AND USE OF OXAZOPYRROLOQUINOLINES

[75] Inventors: Teizi Urakami, Tokyo; Mitsunori Oda, Niigata; Chieko Itoh, Niigata; Hisao Kobayashi, Niigata; Toshio Nagai, Niigata; Kazuhiro Sugamura, Niigata, all of Japan

[73] Assignee: Mitsubishi Gas Chemical Company, Tokyo, Japan

[21] Appl. No.: 60,240

[22] Filed: Jul. 12, 1993

Related U.S. Application Data

[60] Division of Ser. No. 826,220, Jan. 23, 1992, Pat. No. 5,236,930, which is a continuation of Ser. No. 609,807, Nov. 6, 1990, abandoned.

[30] Foreign Application Priority Data

| Nov. 13, 1989 | [JP] | Japan | 1-292459 |
| Nov. 29, 1989 | [JP] | Japan | 1-309480 |
| Dec. 19, 1989 | [JP] | Japan | 1-327347 |
| Apr. 12, 1990 | [JP] | Japan | 2-94962 |
| Jun. 28, 1990 | [JP] | Japan | 2-168483 |
| Aug. 3, 1990 | [JP] | Japan | 2-205103 |

[51] Int. Cl.⁶ ............... A61K 31/435; C07D 498/14; C12P 17/18; C12P 17/16

[52] U.S. Cl. .............. 435/119; 435/118; 435/822; 435/863; 514/287; 546/64

[58] Field of Search ............. 435/119, 118, 822, 863; 514/287; 546/64

[56] References Cited

U.S. PATENT DOCUMENTS

4,994,382 2/1991 Ameyama et al. ............. 435/119

*Primary Examiner*—Herbert J. Lilling
*Attorney, Agent, or Firm*—Henry T. Burke

[57] ABSTRACT

The present invention provides a process for producing oxazopyrroloquinolines which comprises culturing microorganisms to produce pyrroloquinolinequinone and adding α-amino acids or monomethylamine to the resulting culture broth which contains the pyrroloquinolinequinone and from which cells of microorganisms are not separated, thereby to convert the pyrroloquinolinequinone to the corresponding oxazopyrroloquinolines. The thus obtained oxazopyrroloquinolines include novel compounds. The present invention further provides aldose reductase inhibitors, diabetic combined disease curing agents, immunopotentiating agents and liver disease inhibiting agents which contain as active ingredient these oxazopyrroloquinolines having excellent physiological activity.

3 Claims, No Drawings

PROCESS FOR PRODUCING OXAZOPYRROLOQUINOLINES, NOVEL OXAZOPYRROLOQUINOLINES, AND USE OF OXAZOPYRROLOQUINOLINES

This application is a divisional application of application Ser. No. 07/826,220, filed Jan. 23, 1992, now U.S. Pat. No. 5,236,930, which is a continuation of Ser. No. 07/609,807, filed Nov. 6, 1990, now abandoned.

The present invention relates to a process for producing oxazopyrroloquinolines and more particularly it relates to a process for producing oxazopyrroloquinolines from pyrroloquinoline quinone obtained using microorganisms. It further relates to novel oxazopyrroloquinolines and use of oxazopyrroloquinolines.

Oxazopyrroloquinolines also known as 5-substituted 2,8,10-tricarboxy-1H-oxazo[5,4-h]-pyrrolo[2,3-f]quinoline (hereinafter genetically referred to as "OPQs") and have the following chemical structural formula [I]:

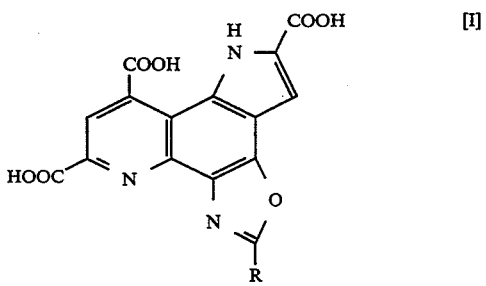

wherein R represents hydrogen or a lower alkyl group having 1 to 4 carbon atoms which may be substituted by substituent(s), selected from the group consisting of hydroxyl, carboxyl, mercapto, amino, carbamoyl, phenyl, hydroxyphenyl, guanidino, imidazolyl and, methylmercapto groups.

OPQs are derivatives of pyrroloquinolinequinone (hereinafter referred to as "PQQ") and are important compounds which are to be developed as medicines in the future. PQQ was found as a coenzyme for methanol dehydrogenase of methanol utilizing microorganisms.

PQQ exists not only in microorganisms, but also in fungi of eukaryote, yeast, and mammals and bears important function as coenzyme. Furthermore, it has been clarified that PQQ has various physiological activities such as cell propagation-promoting action (Japanese Patent Kokai Nos. 61-58584and 63-233783), anticataract action (Japanese Patent Kokai Nos. 63-41421, 63-48215, and 64-29313), liver disease preventive-therapeutic action (Japanese Patent Kokai No. 63-192717), wound healing (Japanese Patent Kokai No. 63-152309), antiallergic action (Japanese Patent Kokai No. 63-17493),reverse transcriptase-inhibiting action (Japanese Patent Kokai Nos. 63-156724 and 1-29313), and glyoxalase I inhibiting action-carbinostatic action (Japanese Patent Kokai Nos. 63-215628 and 1-29313).

However, it has been clarified recently that PQQ has toxicity to kidney (Watanabe et al. "Hiroshima J. Med. Sci.", Vol. 38, No. 1, pages 49–51 (1989)), and development of safe PQQ derivatives which are low in both general toxicity and toxicity to kidney has been desired.

The inventors have conducted tests for toxicity to kidney and acute toxicity test on various PQQ derivatives to find that oxazopyrroloquinolines (OPQs) markedly diminished these toxicities.

It is known that OPQ (R=H in the above formula) can be obtained by allowing PQQ to react with glycine. (Collection of Abstract of Presentation in Japan Chemical Society 2III B34 (1989)). However, PQQ of high purity free from impurities is used in this process. PQQ is usually produced using microorganisms and the culture solution obtained contains various foreign materials, e.g., cell, substances in microorganism, such as proteins and saccharides, components of culture medium and by-products in large amounts. These foreign materials may have an adverse effect on reaction. Furthermore, after completion of fermentation production of PQQ, the PQQ rapidly reacts with protein and other products and thus is consumed. In order to inhibit this consumption of PQQ, PQQ is rapidly separated and recovered from the culture broth and, if necessary, is purified and used for production of OPQ.

However, separation and recovery of PQQ from culture broth and purification thereof require troublesome steps. Besides, since the content of PQQ in culture broth is very low, further complicated steps are necessary for efficient separation and purification of PQQ. Use of PQQ of high purity thus obtained causes a bottleneck in the industrial production of OPQ.

In general, aldose reductase is an enzyme which reduces glucose to sorbitol in the presence of NADPH. This sorbitol is converted to fructose by sorbitol dehydrogenase in the presence of NAD. The route of conversion of glucose to fructose through sorbitol is called polyol metabolism.

Glucose is an important substance as an energy source. Under normal conditions, glucose is entrapped in cells and thereafter most of it is converted to glucose-6-phosphoric acid by the action of hexokinase and metabolized by glycolytis pathway and thus only a small percent of glucose is metabolized through the polyol route. However, when high blood sugar state occurs due to diabetes, concentration of glucose in cells of insulin-non-dependent tissues such as peripheral nerve, retina, crystalline lens, cornea, vascular tract, renal glomerulus, and erythrocyte increases and glucose metabolism through polyol route is accelerated and excess sorbitol is produced. This sorbitol is high in polarity and so is inferior in diffusion through the cell wall. Therefore, it is considered that there are caused diabetic associated diseases such as diabetic neurosis, diabetic retinitis, diabetic cataract, diabetic keratitis, and diabetic renal diseases, etc.

Therefore, prevention and curing of diabetic diseases should be possible by inhibiting aldose reductase. Various aldose reductase inhibitors have been studied and developed, but none of them cannot be put to practical use.

Furthermore, it has been reported that pyrroloquinolinequinone (PQQ) and pyrroloquinolinequinone salts (hereinafter generically referred to as "PQQs") found recently as novel coenzymes of oxidoreductase inhibit aldose reductase. (Japanese Patent Kokai Nos. 63-41421 and 63-48215). However, the activity thereof is still insufficient moreover as mentioned above, it has been recently established that PQQ has kidney toxicity.

No agents for curing the above-mentioned diabetes associated diseases by inhibiting aldose reductase have become practical to use.

In general, elderly people weaken in their immunological response to foreign invaders such as bacteria, and are susceptible to infection with weak pathogenic microorganisms such as colon bacilli. Especially, those who have had a surgical operation are often infected with these pathogenic microorganisms and die of acute pneumonia. This is serious problem in care of aged people who have undergone surgical operation.

Humoral and cellular immune systems play an important role in defense against infection with bacteria, yeast, fungi, and virus, and in the defense mechanism of the living body against tumor.

Macrophage plays an important role in removal of foreign substances and in specific immunity in living body. Removal of pathogenic microorganisms and tumor cells is effected by the by immune response of T cells of lymphocytes and production of antibody by B cell of lymphocytes.

Furthermore, it is also understood that these immune systems participate in the removal of cells which are damaged in the course of aging. Thus, development of immunopotentiating agents has been conducted not only for inhibition of infection or tumor, but also in convection to the phenomenon of aging. Satisfactory medicines have not yet been developed.

The liver is an important organ which controls most of metabolism in a living body and performs metabolism of saccharides, proteins, lipids, nucleic acids, vitamins, and hormones production of bilirubin, secretion of bile, detoxification of internal and external substances by oxidation, reduction and conjugation and excretion of them into bile or water-solubilization of them to accelerate excretion into urine. These functions may be damaged by toxic substances, medicines, alcohols, radiation and virus to cause diseases such as medicinal liver disease, alcoholic liver diseases, virus-caused hepatitis, fatty liver, jaundice, and the like. If these diseases are protracted, sometimes liver cirrhosis and cancer of liver develop.

Medicines effective to cure these liver diseases have not yet been developed and at present, treatments therefor are only dietetic therapy and resting therapy.

On the other hand, recently, it has been reported that pyrroloquinoline quinone and pyrrolo quinoline quinone salts found as novel coenzymes of oxidoreductase inhibit liver diseases (Japanese Patent Kokai No. 63-192717).

Thus, development of medicines low in general toxicity, specific toxicity to kidney and having inhibition action on liver diseases has been desired.

An object of the present invention is to provide a process for efficiently and stably producing OPQs or salts thereof.

Another object of the present invention is to provide novel OPQs.

Still another object of the present invention is to provide an aldose reductase inhibitor, a therapeutic agent for diabetic combined diseases, an immunopotentiating agent and liver disease inhibitor very low in general toxicity and specific toxicity to kidney.

As a result of intensive research conducted by the inventors on production of OPQs by culturing of microorganisms, it has been found that when a microorganism capable of producing PQQ is cultured in a medium with methanol as a carbon source to accumulate PQQ in culture broth and then at least one of various amino acids and monomethylamine is added to the culture broth and PQQ is allowed to react with these compounds in the presence of oxygen, the PQQ accumulated in the culture broth is efficiently converted to OPQs. These OPQs include novel compounds, which have excellent physiological activities and can be employed for various uses.

The present invention is a process for producing oxazopyrroloquinolines, characterized in that a microorganism capable of producing pyrroloquinolinequinone is cultured in a medium with methanol as a carbon source to obtain a culture broth containing pyrroloquinolinequinone, and at least one of various amino acids and monomethylamine is added to the culture broth in the presence of oxygen to convert the pyrroloquinoinequinone in the culture broth to oxazopyrroloquinolines.

In the present invention, any microorganisms can be used which have methanol utilizing ability and have ability to produce PQQ extra cellularly Representative examples of strains of these microorganisms are as follows.

1. Genus Methylobacillus

*Methylobacillus glycogenes* ATCC 29475 (=JCM 2850=NCIB 11375), ATCC 21275 (=JCM 2841), ATCC 21452 (=JCM 2842), ATCC 21961 (=JCM 2843), ATCC 21852 (=JCM 2840=NCIB 11376), ATCC 21369 (=JCM 2844), ATCC 21958 (=JCM 2847), ATCC 21963 (=JCM 2848), ATCC 21370 (=JCM 2849), ATCC 21372 (=JCM 2852), ATCC 21959, ATCC 21371 (=JCM 2853), ATCC 21957 ATCC 21276 (=JCM 2854), ATCC 21453 (=JCM 2855), ATCC 21962 (=JCM 2856), ATCC 21704 (=JCM 2857), ATCC 21960 (=JCM 2858), ATCC 21439, NCIB 10508 (=JCM 2859), NCIB 10509, NCIB 10510 (=JCM 2860), NCIB 10511, NCIB 10512 (=JCM 2861), NCIB 10513, NCIB 10514, NCIB 10592 (=JCM 2862), NCIB 10593, NCIB 10594 (=JCM 2863), NCIB 10595, NCIB 10596 (=JCM 2864), JCM 2851 (=NRRL B-5458), JCM 2866, FERM P-1692, FERM P-1693, FERM P-1694, FERM P-2182, FERM P-2184, FERM P-2247, FERM P-2661, FERM P-2662, FERM P-2663, FERM P-4036, FERM P-4037, FERM P-4038, FERM P-4039., FERM P-4040, FERM P-4041, FERM P-4042 and FERM P-4043. (Names of the species are based on International Journal of Systematic Bacteriology, Vol. 36, pages 502-511 (1986)).

2. Genus Methylophilus:

*Methylophilus methylotrophus* NCIB 10515 and ATCC 31226 (=NCIB 11809). (Names of the species are based on International Journal of Systematic Bacteriology, Vol. 37, pages 446-448 (1987))

3. Genus Methylobacterium

*Methylobacterium extorquens* DSM 1337 (=JCM 2802=NCIB 9399), JCM 2803 (=NCIB 10409), ATCC 8457 (=DSM 1340=IAM 1081=JCM 2804=NCIB 2879), ATCC 14718 (=DSM 1338=JCM 2805=NCIB 9133), DSM 1339 (=JCM 2806=NCIB 9686) and NCIB 10409;

*Methylobacterium rhodinum* ATCC 14821 (=JCM 2811=NCIB 9421);

*Methylobacterium rhodesianum* NCIB 12249, ATCC 21611 (=JCM 2807), ATCC 21612 (=JCM 2808), ATCC 21613 (=JCM 2809), ATCC 21614 (=JCM 2810), NCIB 10597, NCIB 10598 (=JCM 2812), NCIB 10599 (=JCM 2813), NCIB 10600 (=JCM 2814), NCIB 10601 (=JCM 2817), NCIB 10602 (=JCM 2815) and NCIB 10611 (=JCM 2816);

*Methylobacterium zatmanii* NCIB 12243, NCIB 10603 (=JCM 2818), NCIB 10604 (=JCM 2825), NCIB 10606 (=JCM 2819), NCIB 10607 (=JCM 2820) NCIB 10608 (=JCM 2821), NCIB 10609 (=JCM 2822) NCIB 10610 (=JCM 2823) and NCIB 10612 (=JCM 2824);

*Methylobacterium organophilum* ATCC 27886 (=JCM 2833);

*Methylobacterium mesophilius* ATCC 29983 (=JCM 2829 =NCIB 11561);

*Methylobacterium fujisawaensis* NCIB 12417 and NCIB 11272;

*Methylobacterium radiotolerans* IAM 12099 (=ATCC 27329=JCM 2830=NCIB 10815), IAM 12098 (=JCM 2831), NCIB 9142 and NCIB 9143; and Methylobacterium SP. ATCC 21438 (=JCM 2827), IAM 12623 (=JCM 2834), JCM 2832, NCIB 9141, NCIB 9145, NRRL B-3449, FERM P-4893, FERM P-4894, FERM P-4895, FERM P-4896, FERM P-4897 and FERM P-9466. (Names of species are based on International Journal of Systematic Bacteriology, Vol. 33, pages 875–877 (1983) and Vol 38, pages 124–127 (1988)).

4. Genus Ancylobacter

*Ancylobacter aquaticus* ATCC 25396 (=CCM 1786=DSM 101=NCIB 9271), ATCC 27068 (=DSM 334), ATCC 27069, ATCC 21373 (=DSM 1106), NCIB 10516 (=DSM 2457), DSM 2666 (=FERM P-4416), DSM 26.67 (=FERM P-4417), DSM 2668 (=FERM P-4418) and DSM 2669 (=FERM P-4419); and Ancylobacter sp. DSM 1107, DSM 1108, DSM 1277, DSM 2455 and DSM 2456. (Names of species are based on International Journal of Systematic Bacteriology, Vol. 36, pages 415–421 (1986))

5. Genus Hyphomicrobium

*Hyphomicrobium vulgare* NCIB 9698, NCIB 9775, DSM 1564, NCIB 11052, NCIB 9696, DSM 1566, NCIB 9697, NCIB 9699, NCIB 10099, NCIB 10342 (=DSM 1565) and NCIB 11053; and

*Hyphomicrobium methylovorum* IFO 14180, NCIB 10517 and DSM 1869 (=NCIB 11706) (Names of species are based on Journal of Applied Microbiology, Vol. 33, pages 521–542 (1987))

6. Genus Xanthobacter

*Xanthobacter autotrophicus* DSM 432, DSM 431, DSM 685, DSM 1393, DSM 1618, DSM 2009 and DSM 2267; and

*Xanthobacter flavus* DSM 338 (=NCIB 10071) (Names of species are based on International Journal of Systematic Bacteriology, Vol. 28, pages 573–581 (1981))

7. Genus Acidomonus

*Acidomonus methanolica* JCM 6891 (=IMET 0945) and JCM 3712 (=FERM P-2664) (Names of species are based on International Journal of Systematic Bacteriology, Vol. 39, pages 50–55 (1989))

8. Genus Paracoccus

*Paracoccus denitrificans* ATCC 17441 (=DSM 65=IAM 12479=NCIB 11627), ATCC 13543 (=CCM 982=NRRL B-3784), ATCC 19367 (=DSM 413=IFO 13301=NCIB 8944=NRRL B-3785), CCM 1396 (=DSM 415=NCIB 9722) and IFO 12442; and

*Paracoccus alcaliphilus* JCM 7364 (=FERM P-9282), FERM P-9280 and FERM P-9281 (Names of species are based on International Journal of Systematic Bacteriology .Vol. 39, pages 116–121 (1989))

9. Genus Thiobacillus

*Thiobacillus novellus* ATCC 8093 (=CCM 1077 =DSM 506=IFO 12443=NCIB 9113) and NCIB 10456. (Names of species are based on International Journal of Systematic Bacteriology, Vol. 30, pages 225–420 (1980))

10. Genus Methylophaga

*Methylophaga marina* ATCC 35842 (=NCMB 2244);

*Methylophaga thalassica* ATCC 33146 (=IAM 12458=NCMB 2163), NCMB 2162 (=FERM P-3622) and ATCC 33145; and Methylophaga sp. FERM P-3619, FERM P-3620, FERM P-3623 and FERM P-3624 (Names of species are based on International Journal of Systematic Bacteriology, Vol. 37, pages 402–406 (1982))

11. Genus Mycobacterium

*Mycobacterium methanolica* FERM P-8823, FERM P-8824, FERM P-8825, FERM P-8826, FERM P-8827, FERM P-9464, FERM P-9465 and FERM P-9497. (The microbiol ogical properties of these strains belonging to Genus Mycobacterium are mentioned in Japanese Patent Kokai Nos. 63-28385, 64-51077, and 64-60371.)

These strains are all known.

Mutants obtained from these strains can also be used.

It is necessary that nutrient media used for culturing these PQQ producing microorganisms contain methanol as the main carbon source. Furthermore, suitable amounts of nitrogen inorganic sources are used as medium components.

Normally, for example, ammonium sulfate, urea, ammonium nitrate, and ammonium phosphate are used as nitrogen source and phosphates, magnesium salts, iron salts as inorganic salts and, if necessary, trace metal salts are used. Furthermore, when the strain used shows auxotrophy, it is necessary to add the nutrient substance to the medium.

Since Methylophaga microorganisms require NaCl for growing, it is necessary to add NaCl to medium in an amount of 2–4% by weight or to use seawater as water used for forming the medium.

The culturing temperature, suitable for growth and propagation of respective strains is normally about 25°–45° C.

The pH range for culturing, growth and propagation of respective strains is from the about 6–8. However, since pH for growth of Acidomonus microorganisms is 2.0–5.5 and pH for growth of strain of *Paracoccus alcaliphilus* is 7.0–10.0, when these strains are used, it is necessary to select pH within these ranges.

When an ammonium salt is used as nitrogen source, pH of culture broth decreases with growth of cell and it is necessary to control pH of culture broth by adding ammonia, potassium hydroxide, sodium hydroxide, or the like in order to control the pH of culture broth during culturing: Ammonia is especially preferred.

PQQ is produced in culture broth by aerobic culture by the methods such as aerated culture.

To this culture broth is added at least one of α-amino acids and monomethylamine to allow the compound to react with PQQ contained in the culture broth in the presence of oxygen to obtain OPQs corresponding to the amino acid or monomethylamine used.

The α-amino acids used here are represented by R-CH(NH$_2$)-COOH. [Wherein R represents hydrogen or a lower alkyl group having 1 to 4 carbon atoms which may be substituted by substituent(s), said substituent(s) being selected from the group consisting of hydroxyl, carboxyl, mercapto, amino, carbamoyl, phenyl, hydroxyphenyl, guanidino, imidazolyl and methylmercapto groups].

Typical examples thereof are glycine, threonine, proline, tryptophan, alanine, valine, leucine, isoleucine, methionine, glutamic acid, phenylalanine, tyrosine, glutamine, serine, aspartic acid, lysine, histidine, arginine, asparagine and cysteine.

They may be used in the D-form, the L-form or mixtures thereof.

Monomethylamine and salts thereof such as hydrochloride can also be used.

These compounds are added to the culture broth in such an amount of at least 1 mole, preferably not less than 5 mole per mole of PQQ contained in the culture broth, when concentration of PQQ in the culture broth reached 10 μg–10 g/l, preferably 100 μg–10 g/l. The more, the better, but practically at least 0.1 g/l.

Normally, the culture broth is used as formed but if necessary, a part of water may be removed by concentration.

pH of the reaction solution varies depending on kind of amino acid and the selected desired OPQs and cannot be generally specified, but practically it is preferably 2–10. The details are mentioned below.

Reaction temperature is preferably about 20°–100° C., most preferably about 25°–80° C.

Reaction time is not critical, but is usually about not more than 48 hrs, preferably about 1–30 hrs.

Concentration of dissolved oxygen in the reaction solution is not critical, but is preferably 0.5–1 ppm or more for terminating the reaction in a short time. For this purpose, of stirring by passing air, oxygen or mixed gas thereof, increasing pressure in reactor may be employed.

The period before addition of the amino acid or monomethylamine to the culture broth is preferably as short as possible and is usually within up to 10 hours, preferably up to 2 hours after completion of fermentation production of PQQ.

OPQ (oxazopyrroloquinoline) (R=H in the formula [I]) is obtained by adding at least one of glycine, tryptophan, proline, threonine, tyrosine, serine and monomethylamine to culture solution and pH for reaction is especially preferably 6–9. Further, 1-methylethyl OPQ (R=CH(CH₃)₂ in the formula [I]) (5-(1-methylethyl)-2,8,10-tricarboxy 1H-oxazo[5,4-h]-pyrrolo[2,3-f]quinoline same hereinafter; "1-methylethyl" given before "OPQ" shows the substituent at 5-position of OPQs and the same is applied to other OPQs) is obtained by adding valine, 1-methlylpropyl OPQ (R=CH(CH₃)CH₂CH₃) is obtained by adding isoleucine, 2-methylpropyl OPQ (R=CH₂CH(CH₃)₂) is obtained by adding leucine, methyl OPQ (R=CH₃) is obtained by adding alanine, 2-carboxyethyl OPQ (R=CH₂CH₂CO₂H) is obtained by adding glutamic acid, 2-carbamoylethyl OPQ (R=CH₂CH₂CONH₂) is obtained by adding glutamine, 2-methylthioethyl OPQ (R=CH₂CH₂SCH₃) is obtained by adding methionine, benzyl OPQ

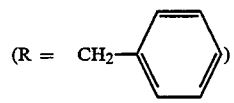

is obtained by adding phenylalanine, carboxymethyl OPQ (R=CH₂CO₂H) is obtained by adding aspartic acid, carbamoylmethyl OPQ

is obtained by adding asparagine, 1-(4-imidazolyl)-methyl OPQ

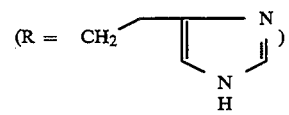

is obtained by adding histidine, 4-aminobutyl OPQ (R=(CH₂)₄NH₂) is obtained by adding lysine, 3-guanidinopropyl OPQ

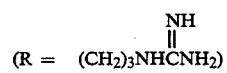

is obtained by adding arginine, and mercaptomethyl OPQ (R=CH₂SH) is obtained by adding cystine to culture broths containing PQQ, respectively. In this case, pH in reaction is especially preferably 6–9.

Furthermore hydroxymethyl OPQ (R=CH₂OH) is obtained by adding serine to the culture broth and by adjusting pH in reaction to 2–6, most preferably 4–6. When pH exceeds 6, OPQ (R=H) is obtained.

4-Hydroxybenzyl OPQ

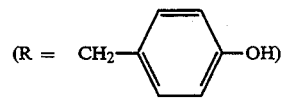

is obtained by adding tyrosine to the culture solution and adjusting pH in reaction to 4–8, most preferably 6–8. When pH exceeds 8, OPQ (R=H) is obtained.

Salt of OPQs can be obtained by adding an alkali corresponding to the desired salt of OPQs to a culture containing OPQs.

From the thus obtained reaction mixture, solid materials such as cells are removed by usual solid-liquid separation means such as filtration and centrifugation to obtain a supernatant liquid.

In the case of producing OPQs at a low pH of 3–5, the produced OPQs may be present as a precipitate in the reaction mixture. Therefore, it is necessary to once dissolve the produced OPQs adjusting pH of the reaction solution and the reaction mixture, respectively, to from a neutral to alkaline range and then obtain supernatant liquid. OPQs are separated and recovered from the resulting supernatant liquid.

These are various methods for separation and purification of OPQs from the thus obtained supernatant liquid. These include, for example, a method of using resin carrier capable of adsorbing OPQs, an extracting method, a precipitating method, washing method and ultrafiltration method. These methods can be used singly or in combination to separate and purify OPQs.

Methods of separation and purification of OPQs will be explained in more detail.

The precipitation method includes acidic precipitation in which OPQs are precipitated with rendering the reaction mixture acidic by inorganic acids such as hydrochloric acid, sulfuric acid and nitric acid or organic acids such as trichloroacetic acid, trifluoroacetic acid and trifluoromethane-sulfonic acid; the salting-out method in which OPQs are precipitated by adding to the reaction mixture alkali metal salts such as sodium chloride and potassium chloride or alkaline earth metal salts such as calcium chloride and the magnesium chloride; and solvent precipitation method in which OPQs are precipitated by mixing the reaction mixture with a solvent such as acetone in which hydroxymethyl OPQs are low in solubility.

In these precipitation methods, recovery of OPQs increases with decrease in temperature of solution.

Purity of OPQs or precipitates containing OPQs obtained by the above purification method can be further improved by washing with solvents such as acetone, diethyl ether and acidic water which dissolve OPQs with difficulty.

In production of OPQs by fermentation method, removal of foreign materials such as polymers in the culture broth can be carried out by the ultrafiltration method.

For ultrafiltration there may be employed a method which uses resin carriers such as SEPHADEX G-10 (manufactured by Pharmacia Fine Chemicals, Inc.) and TOYOPAL HW series (manufactured by Toso Co.) or a method which uses various ultrafiltration membranes and hollow fibers.

Water, organic solvents, etc. are used as extractants in extraction methods. Organic solvents are preferably those which are low in compatibility with water. Suitable examples are aliphatic alcohols having 4 or more carbon atoms such as n-butanol.

For the method of using a resin carrier capable of adsorbing OPQs, any resin carriers which adsorb and desorb OPQs can be used. Typical examples of the resin carriers, include anion exchange resin carriers such as DEAE-SEPHADEX A-25 (manufactured by Pharmacia Fine Chemicals, Inc.) which is a polysaccharide carrier and DEAE-TOYOPAL 650 (manufactured by Toso Co.) and AMBERLIST A-21 (manufactured by Rohm & Haas Co.) which are hydrophilic polymer resins. Adsorption separation type carriers include DIAION HP series (manufactured by Mitsubishi Chemical Industries, Ltd.) and AMBERLITE XAD series (Rohm & Haas Co.) which are hydrophobic polymer resins silica, octadecyl silica and alumina. Typical hydrophobic resin carriers for chromatography include BUTYL-TOYOPAL 650 and PHENYL-TOYOPAL 650 (manufactured by Toso Co.).

Identification of OPQs is may be by means such as elemental analysis, nuclear magnetic resonance spectrum, infrared absorption spectrum, and mass spectrometry.

Determination of amount of OPQs can be conducted carried out by high performance liquid chromatography.

These OPQs include the following compounds.

(1) Hydroxymethyl OPQ

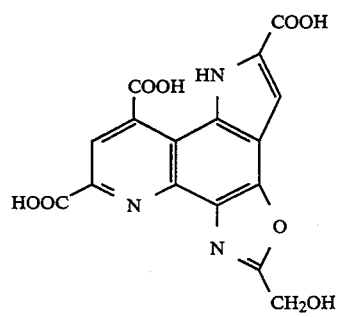

5-Hydroxymethyl-2,8,10-tricarboxy-1H-oxazo[5,4-h]-pyrrolo[2,3-f]-quinoline.

(2) 1-Methylethyl OPQ

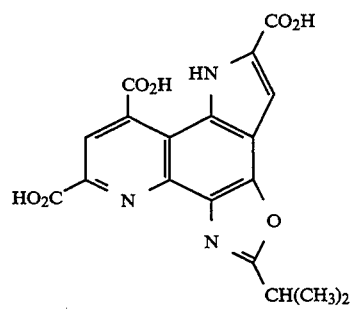

5-(1-Methylethyl)-2,8,10-tricarboxy-1H-oxazo[5,4-h]-pyrrolo[2,3-f]quinoline.

(3) 1-Methylpropyl OPQ

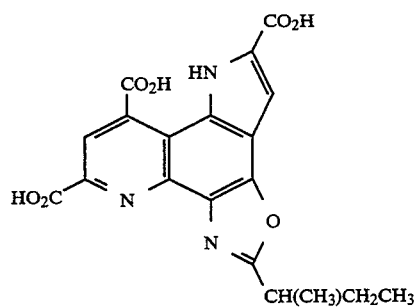

5-(1-Methylpropyl)-2,8,10-tricarboxy-1H-oxazo[5,4-h]-pyrrolo[2,3-f]quinoline.

(4) 2-Methylpropyl OPQ

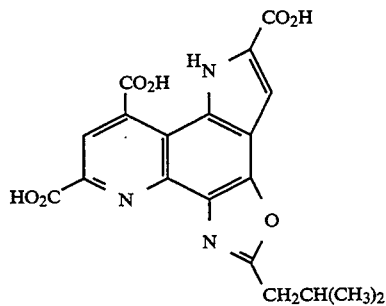

5-(2-Methylpropyl)-2,8,10-tricarboxy-1H-oxazo[5,4-h]-pyrrolo[2,3-f]quinoline.

(5) Methyl OPQ

-continued

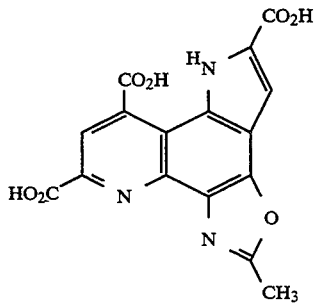

5-Methyl-2,8,10-tricarboxy-1H-oxazo[5,4-h]-pyrrolo-[2,3-f]quinoline.

(6) 2-Carboxylethyl OPQ

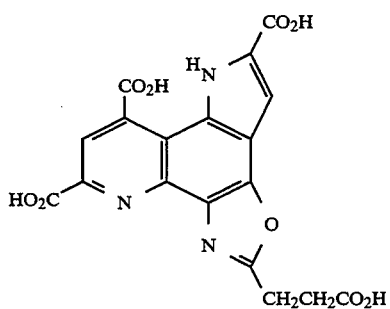

5-(2-Carboxyethyl)-2,8,10-tricarboxy-1H-oxazo[5,4-h]-pyrrolo[2,3-f]quinoline.

(7) 2-Carbamoylethyl OPQ

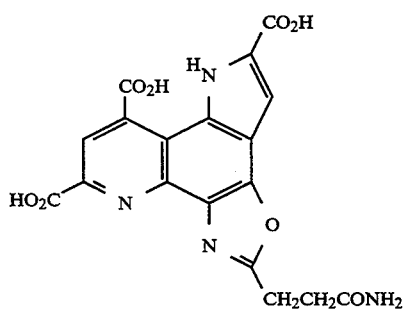

5-(2-Carbamoylethyl)-2,8,10-tricarboxy-1H-oxazo[5,4-h]-pyrrolo[2,3-f]quinoline.

(8) 2-Methylthioethyl OPQ

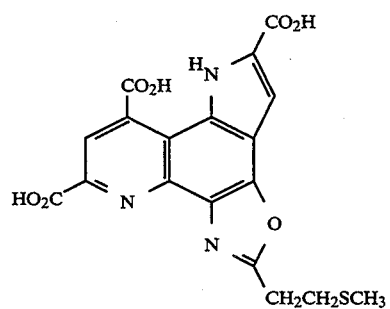

5-(2-Methylthioethyl)-2,8,10-tricarboxy-1H-oxazo-[5,4-h]-pyrrolo[2,3-f]quinoline.

(9) Benzyl OPQ

-continued

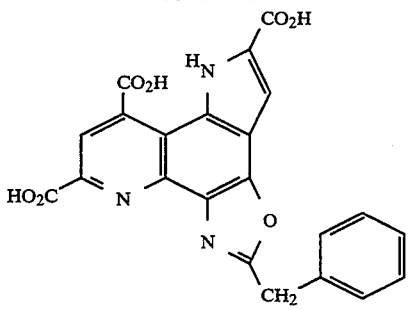

5-Benzyl-2,8,10-tricarboxy-1H-oxazo[5,4-h]-pyrrolo-[2,3-f]-quinoline.

(10) 4-Hydroxybenzyl OPQ

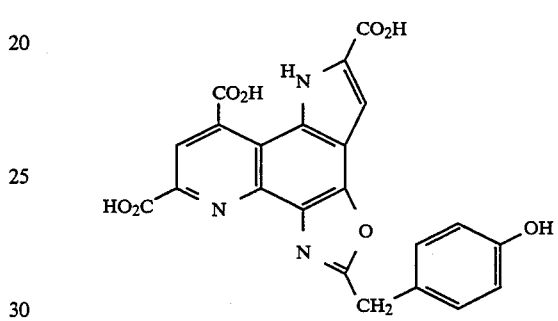

5-(4-Hydroxybenzyl)-2,8,10-tricarboxy-1H-oxazo[5,4-h]-pyrrolo[2,3-f]quinoline.

These novel compounds can be produced using microorganisms as mentioned above and can also be produced by using previously separated and purified PQQ. That is, the desired OPQs can be obtained by allowing PQQ or salts of PQQ to react with the same amino acid corresponding to the desired OPQs or monomethylamine in the presence of oxygen. The amounts of amino acid or monomethylamine and reaction conditions such as temperature and pH are the same as those in the method which uses microoraganism.

Salts of these PQQ compounds include alkali metal salts, alkaline earth metal salts, ammonium salts and substituted ammonium salts.

Examples of the substituted ammonium salts are alkyl substituted ammonium salts and hydroxyalkyl substituted ammonium salts.

Typical examples of the salts of OPQs are sodium salts, potassium salts, magnesium salts, calcium salts, ammonium salts, trimethylammonium salts, triethylammonium salts, and triethanolammonium salts.

The present invention further relates to novel uses of OPQs.

These uses include aldose reductase inhibitors, diabetes associated disease therapeutic agents, immunopotentiating agents and liver disease inhibitors which contain the compounds (OPQs) represented by the following formula I or salts thereof as an active ingredient.

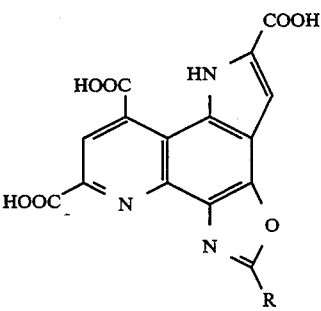

[I]

wherein R represents hydrogen or a lower alkyl group having 1 to 4 carbon atoms which may be substituted by substituent(s) selected from the group consisting of hydroxyl, carboxy, mercapto, amino, carbamoyl, phenyl, hydroxyphenyl, guanidino, imidazolyl and methylmercapto groups.

OPQs and salts thereof used in the present invention may be those which have the above formula [I] where R may be the same as R' of α-amino acid represented by the formula R'—CH$_2$(NH$_2$)—COOH, but preferably is the same as R' of natural α-amino acid, more preferably is the same as R' of α-amino acid which constitutes natural protein.

Typical examples of OPQs are OPQ, hydroxymethyl OPQ, 1-methylethyl OPQ, 1-methylpropyl OPQ, 2-methylpropyl OPQ, methyl OPQ, 2-carboxyethyl OPQ, 2-carbamoylethyl OPQ, 2-methylthioethyl OPQ, benzyl OPQ, 4-hydroxybenzyl OPQ, carboxymethyl OPQ, carbamoylmethyl OPQ, 4-imidazolylmethyl OPQ, 4-aminobutyl OPQ, 3-guanidinopropyl OPQ, and mercaptomethyl OPQ.

Typical examples of salts of OPQs are sodium salts, potassium salts, magnesium salts, calcium salts, ammonium salts, trimethylammonium salts, triethylammonium salts and triethanolammonium salts.

For aldose reductase inhibitor and diabetes associated disease therapeutic agents, esters represented by the following formula [II] may be used besides the above-mentioned compounds.

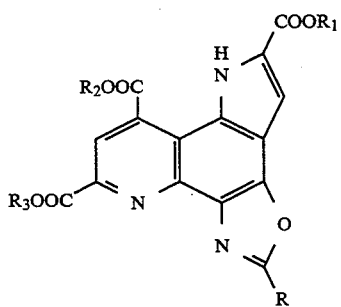

[II]

wherein R represents hydrogen or a lower alkyl group having 1 to 4 carbon atoms which may be substituted by substituent(s) selected from the group consisting of hydroxyl, carboxy, mercapto, amino, carbamoyl, phenyl, hydroxyphenyl, guanidino, imidazolyl and methylmercapto groups and $R^1$, $R^2$ and $R^3$ which may be identical or different, each represents a hydrogen atom, an alkyl group, an alkenyl group or a benzyl group.

The esters used in the present invention may be any of monoesters, diesters and triesters. These esters of OPQs can be easily produced by allowing OPQs or salts thereof and alcohols to react with each other by conventional procedures. The alkyl groups include, for example, methyl group, ethyl group and the like and the alkenyl group includes, for example, allyl group and the like.

Alternatively, the desired esters of OPQs can be obtained by allowing PQQ or PQQ salt to react with alcohols by conventional means to obtain esters of PQQs and then allowing the esters of PQQs to react with various amino-acid or methylamine.

As aldose reductase inhibitor, diabetes associated disease therapeutic agent, imunopotentiating agent and liver disease inhibitor of the present invention, OPQs or salts thereof or esters thereof can be in either parenteral or non-parenteral formulations including a pharmaceutically acceptable carrier. In the case of oral administration, they can be administered in the conventional formulations such as capsules, tablets, and powders. In the case of non-oral administration, they are administered in the formulations such as injection and liquid. Administration in the form of slow release compositions is also effective. For formulation of active ingredients of the present invention, there may be optionally used surface active agent, vehicle, colorant, preservative, coating aid, and the like. Furthermore, they may be used in combination with other medicines.

Dosage thereof may vary depending on kind of disease, condition of disease, kind of OPQs and manner of administration, normally 1–100 mg, preferably 5–50 mg/kg(body weight)/day. The agents of the above dosage are administered once or with divided administration in twice or three times a day.

According to the present invention, OPQs including novel compounds and salts thereof can be efficiently and stably produced. These OPQs, and salts thereof and esters thereof are very low in toxicities such as acute or chronic toxicity and toxicity to kidney and can be effectively used as aldose reductase inhibitor, diabetes associated disease therapeutic agent and liver disease therapeutic agent.

Moreover, uses-of these OPQs and salts thereof as other medicines, medicines for animals and agricultural agents such as pollen germination promoting agent and pollen tube elongation promoting agent can be expected.

The compounds of the invention have immunopotentiating action to enhance activity of B cell, T cell and macrophage and so are utilized not only for inhibition of various infections and tumors, but also as preventive and therapeutic agent against diseases caused by aging.

[Test on acute toxicity and toxicity to kidney of PQQ and OPQs]

(1) Acute toxicity test:

(i) To male SPF-ICR mice 5 weeks old (supplied by Charles River Co.) were intraperitoneally administered PQQ.2Na and OPQs in the dosages of 20, 40, 80, 160 and 200 mg/kg body weight of mouse, respectively and they were bred at 25° C. for 14 days. OPQ, 1-methylpropyl OPQ, 2 -methylthioethyl OPQ, and benzyl OPQ were used as the OPQs. One group consisted of 8 mice. As a result, when 20 mg/kg and 40 mg/kg of PQQ.2Na were administered, the mice survived but five mice died with administration of 80 mg and all of eight mice died with administration of 160 mg and 200 mg.

LD$_{50}$ of PQQ.2Na was about 70 mg/kg mouse.

On the other hand, no mice died with administration of OPQs.

(ii) To male SPF-ICR mice 5 weeks old (supplied by Charles River Co.) was intraperitoneally administered OPQ in the dosages of 0.1, 0.2, 0.4, 0.8 or 1.2 g/kg body weight of mouse and they were bred at 25° C. for 14 days. One group consisted of 8 mice. All mice survived the administration of 0.1–0.4 g, two mice died with administration of 0.8 g, and six mice died with administration 1.2 g. $LD_{50}$ was about 1.0 g/kg mouse.

(iii) To male SPF-ICR mice 5 weeks old (supplied from Charles River Co.) was orally administered OPQ in a dosage of 1.0 g, 1.5 g or 2.0 g/kg mouse. They were bred at 25° C. for 14 days. One group consisted of eight mice.

No mice died.

From the results of (i)–(iii), it can be seen that OPQs are much lower in toxicity than PQQ.

(2) Toxicity to kidney (i) Toxicity to kidney determined by urine examination:

In the same manner as in the acute toxicity test, PQQ.2Na and OPQs were respectively intraperitoneally administered to mice and these mice were bred. Urine was collected every day and concentration of glucose in urine was obtained using Uristex II (manufactured by Miles-Sankyo Co.). As shown in Table 1, sugar was detected from urine of mice to which PQQ.2Na was administered, but no sugar was detected from urine of mice to which OPQs were administered.

That is, PQQ showed toxicity to kidney, but OPQs showed no toxicity to kidney.

TABLE 1

| Administration | Elapsed time (day) | | | | | | | | |
|---|---|---|---|---|---|---|---|---|---|
| of compound | 1 | 2 | 3 | 6 | 7 | 8 | 10 | 13 | 14 |
| No administration | − | − | − | − | − | − | − | − | − |
| PQQ.2Na | | | | | | | | | |
| 20 mg/kg | − | − | − | − | − | − | − | − | − |
| 40 mg/kg | 3+ | 4+ | 4+ | 3+ | ± | ± | ± | ± | − |
| 80 mg/kg | 4+ | 4+ | 4+ | 3+ | + | ± | − | − | − |
| OPQ | | | | | | | | | |
| 20 mg/kg | − | − | − | − | − | − | − | − | − |
| 40 mg/kg | − | − | − | − | − | − | − | − | − |
| 80 mg/kg | − | − | − | − | − | − | − | − | − |
| 160 mg/kg | − | − | − | − | − | − | − | − | − |
| 200 mg/kg | − | − | − | − | − | − | − | − | − |
| 400 mg/kg | − | − | − | − | − | − | − | − | − |
| 800 mg/kg | − | − | − | − | − | − | − | − | − |
| 1000 mg/kg | − | − | − | − | − | − | − | − | − |
| 1200 mg/kg | − | − | − | − | − | − | − | − | − |
| 1-methylpropyl OPQ | | | | | | | | | |
| 20 mg/kg | − | − | − | − | − | − | − | − | − |
| 40 mg/kg | − | − | − | − | − | − | − | − | − |
| 80 mg/kg | − | − | − | − | − | − | − | − | − |
| 160 mg/kg | − | − | − | − | − | − | − | − | − |
| 200 mg/kg | − | − | − | − | − | − | − | − | − |
| 2-methylethyl OPQ | | | | | | | | | |
| 20 mg/kg | − | − | − | − | − | − | − | − | − |
| 40 mg/kg | − | − | − | − | − | − | − | − | − |
| 80 mg/kg | − | − | − | − | − | − | − | − | − |
| 160 mg/kg | − | − | − | − | − | − | − | − | − |
| 200 mg/kg | − | − | − | − | − | − | − | − | − |
| Benzyl OPQ | | | | | | | | | |
| 20 mg/ka | − | − | − | − | − | − | − | − | − |
| 40 mg/kg | − | − | − | − | − | − | − | − | − |
| 80 mg/kg | − | − | − | − | − | − | − | − | − |
| 160 mg/kg | − | − | − | − | − | − | − | − | − |
| 200 mg/kg | − | − | − | − | − | − | − | − | − |

TABLE 1-continued

| Administration | Elapsed time (day) | | | | | | | | |
|---|---|---|---|---|---|---|---|---|---|
| of compound | 1 | 2 | 3 | 6 | 7 | 8 | 10 | 13 | 14 |
| 200 mg/kg | − | − | − | − | − | − | − | − | − |

− No glucose was detected.
± Glucose 0.10 g/dl
+ Glucose 0.25 g/dl
2+ Glucose 0.50 g/dl
3+ Glucose 1.00 g/dl
4+ Glucose 2.00 g/dl (ii) Toxicity to kidney determined by blood examination:

(a) In the same manner as in acute toxicity test, PQQ.2Na and OPQs were respectively intraperitoneally administered to mice and these mice were bred.

After one day from administration, the mice were fasted (only water was given) and after lapse of 18 hours, blood was collected and serum was obtained therefrom. Glucose, urea nitrogen and creatinine in the serum were examined using FUJI Dry Chemslide (manufactured by Fuji Photo Film Co., Ltd.). The results which were determined by average value for eight mice are shown in Table 2.

Sharp reduction of glucose and urea nitrogen and much increase of creatinine were observed with administration of PQQ.2Na and thus toxicity to kidney was recognized. On the other hand, in the case of administration of OPQs, contents of glucose, urea nitrogen and creatinine were nearly the same as those when no OPQs were administered.

TABLE 2

| Administration of compound (mg/kg mouse) | Glucose (mg/dl) | Urea nitrogen (mg/dl) | Creatinine (mg/dl) |
|---|---|---|---|
| No administration | 78 | 24 | 0.8 |
| PQQ.2Na | | | |
| 20 | 70 | 25 | 0.8 |
| 40 | 60 | 110 | 2.3 |
| 80 | 57 | 130 | 3.4 |
| 160 | 35 | 139 | 4.2 |
| OPQ | | | |
| 40 | 90 | 25 | 0.7 |
| 80 | 86 | 23 | 0.8 |
| 160 | 90 | 27 | 0.7 |
| 200 | 85 | 28 | 0.8 |
| 1-methylpropyl OPQ | | | |
| 40 | 87 | 26 | 0.8 |
| 80 | 104 | 22 | 0.8 |
| 160 | 87 | 27 | 0.8 |
| 200 | 66 | 27 | 0.8 |
| 2-methylthioethyl OPQ | | | |
| 40 | 96 | 26 | 0.8 |
| 80 | 88 | 26 | 0.7 |
| 160 | 97 | 26 | 0.6 |
| 200 | 72 | 26 | 0.7 |
| Benzyl OPQ | | | |
| 40 | 90 | 23 | 0.7 |
| 80 | 87 | 23 | 0.7 |
| 160 | 87 | 26 | 0.7 |
| 200 | 84 | 25 | 0.7 |

(b) In the same manner as in the acute toxicity test, 150 mg, 300 mg, 400 mg or 600 mg/kg was intraperitoneally administered to mice and the mice were bred for one day.

Thereafter, the mice were fasted (with giving only water) and after lapse of 18 hours, blood was collected and serum was obtained therefrom. Contents of glucose, urea nitrogen and creatinine in serum were obtained using FUJI Dry Chemslide. The results were shown by average value for eight mice. The results are shown in Table 3.

For administration of OPQ in all of the above dosages, contents of glucose, urea nitrogen and creatinine were nearly the same as those in the case of administration of no OPQ.

TABLE 3

| Administration of compound (mg/kg mouse) | Glucose (mg/dl) | Urea nitrogen (mg/dl) | Creatinine (mg/dl) |
|---|---|---|---|
| No administration OPQ | 105 | 28 | 0.7 |
| 150 | 106 | 32 | 0.8 |
| 300 | 80 | 29 | 0.8 |
| 400 | 94 | 30 | 0.8 |
| 600 | 74 | 34 | 0.8 |

As can be seen from the results of (a) and (b), PQQ showed toxicity to kidney while OPQs showed no toxicity to kidney.

The following nonlimiting examples will further explain the invention.

Example 1

In one liter of pure water were dissolved 3 g of $(NH_4)_2SO_4$, 1.4 g of $KH_2PO_4$, 2.1 g of $Na_2HPO_4$, 0.2 g of $MgSO_4.7H_2O$, 30 mg of $CaCl_2.2H_2O$, 30 mg of $FeC_6H_5O_7.XH_2O$, 5 mg of $MnCl_2.4H_2O$, 5 mg of $ZnSO_4.7H_2O$, 0.5 mg of $CuSO_4.5H_2O$, 4 mg of thiamine hydrochloride, 4 mg of calcium pantothenate, 20 μg of biotin, and 12 ml of methanol. 200 ml of this solution adjusted to pH 7.1 was put in a conical flask of 1 liter in capacity and sterilized at 120° C. for 20 minutes. This was used as a culture medium.

1 vol % of culture broth of bacterial strains precultured at 30° C. for 2 days using the same medium as above was inoculated in the above medium and subjected to rotary shaking culture to obtain culture broth after 3 days from beginning of culture.

The culture broth was divided into two equal parts. To one of them was added 0.3 g/l of glycine and pH was adjusted to 8.5 and this culture broth was subjected to rotary shaking at 30° C. for 24 hours to obtain a reaction mixture in which OPQ was produced. To another one was added 0.4 g/l of L-serine and pH was adjusted to 4.0 and this culture broth was subjected to rotary shaking at 30° C. for 24 hours to allow a reaction to proceed to obtain a reaction mixture in which hydroxymethyl OPQ was produced. These reaction mixtures were subjected to centrifugation to obtain supernatant liquid and amount of OPQs contained therein was measured.

The results are shown in Table 4.

Amount of OPQs in the reaction mixture was measured by high performance liquid chromatography (same in the following examples).

Device: High performance liquid chromatograph manufactured by Shimadzu Seisakusho Ltd.
Column: YMC ODS A-302 (4.6 mmφ × 150 mm)
Developer: 0.1M $KH_2PO_4$, 0.1M $HClO_4$/$CH_3CN:H_2O=1:9$ (pH 2.5)
Flow rate: 1.5 ml/min
Detector: SHIMADZU SPD-6AV UV-VIS detector (420 nm)

TABLE 4

| Strain | OPQ content (mg/l supernatant liquid) amino acid Glycine (pH 8.5) | Hydroxymethyl OPQ content (mg/l supernatant liquid) L-serine (pH 4.0) |
|---|---|---|
| *Methylobacillus glycogenes* | | |
| ATCC 29475 | 0.1 | 0.1 |
| ATCC 21275 | 0.1 | 0.1 |
| ATCC 21372 | 0.1 | 0.1 |
| ATCC 21371 | 0.1 | 0.1 |
| ATCC 21704 | 0.2 | 0.1 |
| NCIB 10510 | 0.4 | 0.3 |
| FERM P-4036 | 0.1 | 0.1 |
| FERM P-4039 | 0.3 | 0.3 |
| FERM P-2661 | 0.2 | 0.2 |
| FERM P-2247 | 0.4 | 0.4 |
| FERM P-2182 | 0.1 | 0.1 |
| *Methylophilus methylotrophus* | | |
| NCIB 10515 | 0.2 | 0.2 |
| ATCC 31226 | 0.2 | 0.2 |
| *Methylobacterium pxtorquens* | | |
| DSM 1337 | 0.8 | 0.7 |
| NCIB 10409 | 0.7 | 0.7 |
| *Methylobacterium rohdinum* | | |
| ATCC 14821 | 0.7 | 0.7 |
| *Methylobacterium rohdesianum* | | |
| NCIB 12249 | 0.6 | 0.5 |
| *Methylobacterium zatmanii* | | |
| NCIB 12243 | 0.6 | 0.6 |
| *Methylobacterium organophilum* | | |
| ATCC 27886 | 0.5 | 0.5 |
| *Methylobacterium mesophilicus* | | |
| ATCC 29983 | 0.6 | 0.6 |
| *Methylobacterium fujisawaensis* | | |
| NCIB 12417 | 0.5 | 0.5 |
| *Methylobacterium radiotolerans* | | |
| IAM 12099 | 0.6 | 0.5 |
| *Methylobacterium sp.* | | |
| FERM P-9466 | 0.7 | 0.7 |
| FERM P-4893 | 0.6 | 0.6 |
| *Ancylobacter aquaticus* | | |
| ATCC 25396 | 1.3 | 1.2 |
| ATCC 21373 | 0.9 | 0.9 |
| NCIB 10516 | 0.6 | 0.5 |
| DSM 2666 | 0.7 | 0.6 |
| *Ancylobacter sp.* | | |
| DSM 2455 | 0.6 | 0.6 |
| *Hyphomicrobium vurgare* | | |
| NCIB 9775 | 1.4 | 1.4 |
| *Hyphomicrobium metbyiovorum* | | |
| IFO 14180 | 0.5 | 0.5 |
| NCIB 10517 | 0.4 | 0.4 |
| DSM 1869 | 8.2 | 8.1 |
| *Xanthobacter autotrophicus* | | |
| DSM 432 | 1.4 | 1.3 |
| *Xanthobacter flavus* | | |
| DSM 338 | 1.2 | 1.1 |
| *Paracoccus* | | |

TABLE 4-continued

| | Strain | |
|---|---|---|
| | OPQ content (mg/l supernatant liquid) | Hydroxymethyl OPQ content (mg/l supernatant liquid) |
| | amino acid | |
| | Glycine (pH 8.5) | L-serine (pH 4.0) |
| *denitrificans* | | |
| ATCC 19367 | 2.3 | 2.2 |
| IFO 12442 | 1.8 | 1.6 |
| *Thiobacillus novellus* | | |
| NCIB 10456 | 2.5 | 2.4 |
| *Mycobacterium methanolica* | | |
| FERM P-8823 | 0.6 | 0.6 |
| FERM P-9497 | 0.8 | 0.6 |

Example 2

*Acidomonus methanolica* JCM 6891 was cultured for 3 days to obtain a culture broth in the same manner as in Example 1 except using a medium prepared by dissolving in one liter of pure water 3 g of $(NH_4)_2SO_4$, 4 g of $KH_2PO_4$, 0.2 g of $MgSO_4.7H_2O$, 30 mg of $CaCl_2.2H_2O$, 30 mg of $FeC_6H_5O_7.XH_2O$, 5 mg of $MnCl_2.4H_2O$, 5 mg of $ZnSO_4.7H_2O$, 0.5 mg of $CuSO_4.5H_2O$, 4 mg of calcium pantothenate, and 12 ml of methanol 10 and adjusting the pH to 4.5.

The culture broth was divided into two equal parts. To one of them was added 0.3 g/l of monomethylamine hydrochloride and pH was adjusted to 8.5 and this culture broth was subjected to stirring for 24 hours at 30° C. to obtain a reaction mixture in which OPQ was produced.

To another one was added 0.4 g/l of L-serine and pH was adjusted to 4.0 and this culture broth was subjected to rotary shaking at 30° C. for 24 hours to allow a reaction to proceed to obtain a reaction mixture in which hydroxymethyl OPQ was produced.

Each of these reaction mixtures was subjected to centrifugation to obtain supernatant liquid and amount of OPQs contained therein was measured. The results are shown in Table 5.

Example 3

*Paracoccus alcalifilus* JCM 7364 was cultured for 3days to obtain a culture broth in the same manner as in Example 1 except using a medium prepared by dissolving in one liter of pure water 3 g of $(NH_4)_2SO_4$, 1.4 g of $KH_2PO_4$, 2.1 g of $Na_2HPO_4$, 0.2 g of $MgSO_4.7H_2O$, 30 mg of $CaCl_2.2H_2O$, 30 mg of $FeC_6H_5O_7.XH_2O$, 5 mg of $MnCl_2.4H_2O$, 5 mg of $ZnSO_4.7H_2O$, 0.5 mg of $CuSO_4.5H_2O$, 20 µg of biotin, and 12 ml of methanol, sterilizing the solution at 120° C. for 20 minutes, then aseptically adding thereto 10 wt % aqueous $Na_2CO_3$ solution, and adjusting the pH to 9.0.

The culture broth was divided into two equal parts. To one of them was added 0.4 g/l of L-serine and pH was adjusted to 8.5 and this culture broth was stirred at 30° C. for 24 hours to obtain a reaction mixture in which OPQ was produced. To another one was added 0.4 g/l of L-serine and pH was adjusted to 4.0 and this culture broth was stirred at 30° C. for 24 hours to obtain a reaction mixture in which hydroxymethyl OPQ was produced.

Each of these reaction mixtures was subjected to centrifugation to obtain supernatant liquid and amount of OPQs contained therein was measured. The results are shown in Table 5.

Example 4

The bacteria belonging to the genus Methylophaga were cultured for 3 days to obtain a culture broth in the same manner as in Example 1 except using a medium prepared by dissolving in one liter of sea water 3.0 g of $(NH_4)_2SO_4$, 1.4 g of $KH_2PO_4$, 2.1 g of $Na_2HP_4$, 0.2 g of $MgSO_4.7H_2O$ 30 mg of $CaCl_2.2H_2O$, 30 mg of $FeC_6.H_5O_7.XH_2O$, 5 mg of $MnCl_2.4H_2O$, 5 mg of $ZnSO_4.7H_2O$, 0.5 mg of $CuSO_4.5H_2O$, and 12 ml of methanol and adjusting the pH to 7.1.

The culture broth was divided into two equal parts. To one of them was added 0.5 g/l of L-threonine and pH was adjusted to 8.5 and this culture broth was stirred at 30° C. for 24 hours to obtain a reaction mixture in which OPQ was produced. To another one was added 0.4 g/l of D-serine and pH was adjusted to 4.0 and this solution was stirred at 30° C. for 24 hours to obtain a reaction mixture in which hydroxymethyl OPQ was produced.

Each of these reaction mixtures was subjected to centrifugation to obtain supernatant liquid and amount of OPQs contained therein was measured. The results are shown in Table 5.

TABLE 5

| Example | Strain | OPQ content (mg/l culture solution) | Hydroxymethyl OPQ content (mg/l supernatant liquid |
|---|---|---|---|
| 2 | *Acidomonus methanolica* JCM 6891 | (monomethylamine pH 8.5) 0.3 | (L-serine, pH 4.0) 0.3 |
| 3 | *Paracoccus alcalifilus* JCM 7364 | (L-serine, pH 8.5) 0.5 | (L-serine, pH 4.0) 0.4 |
| 4 | *Methylophaga marina* ATCC 35842 | (L-threonine, pH 8.5) 6.3 | (D-serine, pH 4.0) 6.2 |
| | *Methylophaga thalassica* | | |
| | NCMB 2162 | 5.0 | 4.7 |
| | ATCC 33146 | 2.8 | 2.4 |
| | ATCC 33145 | 7.2 | 7.0 |
| | *Methylophaga sp.* FERM P-3623 | 4.8 | 4.6 |

Example 5

In one liter of pure water were dissolved 3.0 g of $(NH_4)_2SO_4$, 1.4 g of $KH_2PO_4$, 2.1 g of $Na_2HPO_4$, 0.2 g of $MgSO_4.7H_2O$, 30 mg of $CaCl_2.2H_2O$, 30 mg of $FeC_6H_5O_7.XH_2O$, 5 mg of $MnCl_2.4H_2O$, 5 mg of $ZnSO_4.7H_2O$, 0.5 mg of $CuSO_4.5H_2O$, and 8 ml of methanol and the solution was adjusted to pH 7.1. 200 ml of this solution was put in a conical flask of 1 liter in capacity and sterilized at 120° C. for 20 minutes. This was used as a culture medium.

*Hyphomicrobium vurgare* NCIB 9775 was inoculated in this medium and was subjected to rotary shaking culture at 30° C. using a rotary shaker at 220 rpm. The resulting culture broth was used as a seed liquor.

15 l of medium prepared by dissolving 1.0 of $(NH_4)_2SO_4$, 1.0 g of $MgSO_4.7H_2O$ and 1.4 g of $KH_2PO_4$ in one liter of pure water was put in a culture tank of 30 l in capacity and was sterilized.

In 10 ml of pure water were dissolved 75 mg of $FeSO_4.7H_2O$, 150 mg of $ZnSO_4.7H_2O$, 150 mg of $CaCl_2.2H_2O$, 150 mg of NaCl, 45 mg of $MnSO_4.4–5H_2O$, 3 mg of $H_3BO_3$, 1.5 mg of $CuSO_4.5H_2O$, 1.5 mg of $COCl_2.2H_2O$, 1.5 mg of KI and 1.5 mg of $(NH_4)_6Mo_7O_{24}.4H_2O$. The resulting mineral solution was sterilized.

After temperature of the culture tank of 30 liter lowered to 30° C., 10 ml of the above mineral solution was aseptically added to the medium in the tank and thereto ammonia water was aseptically further added to adjust pH of culture broth to 6.8.

To this culture tank were aseptically added 150 ml of methanol and 200 ml of the above seed liquor and culture was carried out at an aeration speed of 10 l/min and at 300 rpm and at 30° C. with addition of ammonia water so that pH of culture broth was kept at 6.8.

With growth of microorganism, concentration of methanol in culture broth decreased. Methanol in exhaust gas was detected by analysis by gas chromatography and methanol was supplied so that concentration of methanol in culture broth was kept at 0.1–0.5 % by weight.

In this way, culture was conducted in twelve culture tanks of 30 l in capacity for 10 days and to culture broth in the culture tanks were added (1) 90 g of glycine, (2) 120.g of L-serine, (3) 120 g of D-serine, (4) 150 g of L-threonine, (5) 150 g of D-threonine, (6) 150 g of L-proline, (7) 150 g of D-proline, (8) 210 g of L-tyrosine, (9) 210 g of D-tyrosine, (10) 240 g of L-tryptophan, (11) 240 g of D-tryptophan and (12) 75 g of monomethylamine hydrochloride, respectively and reaction was allowed to proceed for 24 hours with adjusting pH of reaction solution to 8.5 to obtain reaction mixtures.

Content of OPQ in the reaction mixtures is shown in Table 6.

TABLE 6

| Experiment No. | Content of OPQ (mg/l reaction mixture) |
| --- | --- |
| (1) | 168 |
| (2) | 162 |
| (3) | 160 |
| (4) | 154 |
| (5) | 155 |
| (6) | 44 |
| (7) | 51 |
| (8) | 105 |
| (9) | 98 |
| (10) | 126 |
| (11) | 117 |
| (12) | 143 |

Example 6

Culture was carried out for 10 days using seven culture tanks of 30 liters in the same manner as in Example 5 except that *Hyphomicrobium methylovorum* DSM 1869 was used as strain and to the culture broths were added glycine in amounts of (1) 4.5 g, (2) 9.0 g, (3) 15.0 g, (4) 45 g, (5) 75 g, (6) 150 g and (7) 22 g and culture was carried out for further 5 hours with adjusting pH to 8.0 to obtain reaction mixtures.

Contents of OPQ in the reaction mixtures are shown in Table 7.

TABLE 7

| Experiment No. | Content of OPQ (mg/l reaction mixture) |
| --- | --- |
| (1) | 258 |
| (2) | 293 |
| (3) | 303 |
| (4) | 298 |
| (5) | 310 |
| (6) | 298 |

TABLE 7-continued

| Experiment No. | Content of OPQ (mg/l reaction mixture) |
| --- | --- |
| (7) | 316 |

Example 7

In the same manner as in Example 6, *Hyphomicrobium methylovorum* DSM 1869 was cultured for 10 days in eight culture tanks of 30 liters.

Thereafter, pH of culture broth in each culture tank was adjusted to (1) 3.0, (2) 4.0, (3) 5.0, (4) 6.0, (5) 7.0, (6) 8.0, (7) 9.0, or (8) 10.0 and 30 g of glycine was added to the culture broth in each culture tank and then reaction was allowed to proceed for further 3 hours to obtain reaction mixture.

Amount of OPQ obtained by centrifugation of each reaction mixture in the culture tank as it was and amount of OPQ obtained by centrifugation of reaction mixtures of (1)–(5) which had been adjusted to pH 8.5 are shown in Table 8.

TABLE 8

| | Content of OPQ (mg/l separated solution) | |
| --- | --- | --- |
| pH | (A) Centrifugation of reaction mixture as it was | (B) Centrifugation of reaction mixture after adjusted to pH 8.5 |
| (1) pH 3.0 | 12 | 202 |
| (2) pH 4.0 | 179 | 235 |
| (3) pH 5.0 | 298 | 296 |
| (4) pH 6.0 | 293 | 304 |
| (5) pH 7.0 | 300 | 301 |
| (6) pH 8.0 | 298 | — |
| (7) pH 9.0 | 294 | — |
| (8) pH 10.0 | 260 | — |

Example 8

In the same manner as in Example 6, *Hyphomicrobium methylovorum* DSM 1869 was cultured for 10 days in eight culture tanks of 30 liters.

Thereafter, pH of culture broth in each culture tank was adjusted to (1) 2.0, (2) 3.0, (3) 4.0, (4) 5.0, (5) 6.0, (6) 7.0, (7) 8.0, (8) 9.0, or (9) 10.0 and 42 g of L-serine was added to the culture broth in each culture tank and then reaction was allowed to proceed for further 5 hours to obtain reaction mixture.

Amount of OPQ and hydroxymethyl OPQ obtained by centrifugation of each reaction mixture in the culture tank as it was and amount of OPQ and hydroxymethyl OPQ obtained by centrifugation of reaction mixtures which had been adjused to pH 8.5 are shown in Tables 9(1) and (2).

TABLE 9

| | (A) Centrifugation of reaction mixture as it was | (B) Centrifugation of reaction mixture after adjusted to pH 8.5 |
| --- | --- | --- |
| pH | Content of OPQ (mg/l reaction mixture) | |
| (1) pH 2.0 | 3 | 20 |
| (2) pH 3.0 | 5 | 49 |
| (3) pH 4.0 | 7 | 51 |
| (4) pH 5.0 | 11 | 55 |
| (5) pH 6.0 | 146 | 149 |
| (6) pH 7.0 | 258 | 260 |
| (7) pH 8.0 | 283 | — |
| (8) pH 9.0 | 280 | — |

TABLE 9-continued

| pH | (A) Centrifugation of reaction mixture as it was | (B) Centrifugation of reaction mixture after adjusted to pH 8.5 |
|---|---|---|
| (9) pH 10.0 | 258 | — |

| | Amount of hydroxymethyl OPQ accumulated (mg/l reaction mixture) | |
|---|---|---|
| (1) pH 2.0 | 10 | 120 |
| (2) pH 3.0 | 15 | 187 |
| (3) pH 4.0 | 149 | 281 |
| (4) pH 5.0 | 272 | 270 |
| (5) pH 6.0 | 253 | 243 |
| (6) pH 7.0 | 98 | 101 |
| (7) pH 8.0 | 50 | 49 |

Example 9

In the same manner as in Example 6, *Hyphomicrobium methylovorum* DSM 1869 was cultured for 10 days in four culture tanks of 30 liters.

Then, temperature of each culture broth in the culture tanks was adjusted to (1) 20° C., (2) 30° C., (3) 40° C., (4) 50° C., or (5) 70° C. and 48 g of L-threonine was added to each of them and reaction was allowed to proceed for 5 hours with adjusting pH of culture broth to 8.0 to obtain reaction mixtures.

Contents of OPQ in the reaction mixtures are shown in Table 10.

TABLE 10

| Temperature | Content of OPQ (mg/l reaction mixture) |
|---|---|
| (1) 20° C. | 253 |
| (2) 30° C. | 294 |
| (3) 40° C. | 317 |
| (4) 50° C. | 317 |
| (5) 70° C. | 300 |

Example 10

*Methylobacillus glycogenes* FERM P-2247 was cultured in the same manner as in Example 6, 27 g of monomethylamine hydrochloride was added to the culture broth on the 4th day after starting of culture and reaction was allowed to proceed for further 6 hours with adjusting pH of culture broth to 8,0 to obtain reaction mixture, Content of OPQ in the reaction mixture was 220 mg/l.

Example 11

*Paracoccus denitrificans* ATCC 19367 was cultured in the same manner as in Example 6.

42 g of D-serine was added to the culture broth on the 10th day after beginning of culture and reaction was allowed to proceed for 6 hours with adjusting pH of the culture broth to 8,0 to obtain a reaction mixture, Content of OPQ in the reaction mixture was 140 mg/l.

Example 12

*Methylophaga thalassica* ATCC 33146 was cultured in the same manner as in Example 6 except that sea water was used as water for medium, 48 g of D-threonine was added to the culture broth on the 10th day after beginning of culture and reaction was allowed to proceed for 6 hours with adjusting pH of the culture broth to 8,0 to obtain a reaction mixture.

Content of OPQ in the reaction mixture was 163 mg/l.

Example 13

In one liter of pure water were dissolved 3 g of $(NH_4)_2SO_4$, 1.4 g of $KH_2PO_4$, 2.1 g of $Na_2HPO_4$, 0.2 g of $MgSO_4 \cdot 7H_2O$, 30 mg of $CaCl_2 \cdot 2H_2O$, 30 mg of $FeC_6H_5O_7 \cdot H_2O$, 5 mg of $MnCl_2 \cdot 4H_2O$, 5 mg of $ZnSO_4 \cdot 7H_2O$, 0.5 mg of $CuSO_4 \cdot 5H_2O$, and 12 ml of methanol and the solution was adjusted to pH 7.1. 200 ml of this solution was put in a conical flask of 1 liter in capacity and sterilized at 120° C. for 20 minutes. This was used as a culture medium.

*Hyphomicrobium vurgare* NCIB 9775 was inoculated in this medium and was subjected to rotary shaking culture at 30° C. using a rotary shaker at 220 rpm. The resulting culture solution was used as a seed liquor.

15 l of a medium prepared by dissolving 1 g of $(NH_4)_2SO_4$. 1 g of $MgSO_4 \cdot 7H_2O$ and 1.4 g of $KH_2PO_4$ in one liter of pure water was put in a culture tank of 30 l in capacity and was sterilized.

In 10 ml of pure water were dissolved 75 mg of $FeSO_4 \cdot 7H_2O$, 150 mg of $ZnSO_4 \cdot 7H_2O$, 150 mg of $CaCl_2 \cdot 2H_2O$, 150 mg of NaCl, 45 mg of $MnSO_4 \cdot 4-5H_2O$, 3 mg of $H_3BO_3$, 1.5 mg of $CuSO_4 \cdot 5H_2O$, 1.5 mg of $COCl_2 \cdot 2H_2O$, 1.5 mg of KI and 1.5 mg of $(NH_4)_6Mo_7O_{24} \cdot 4H_2O$. The resulting mineral solution was sterilized.

After the temperature of the culture tank lowered to 30° C., 10 ml of the mineral solution was aseptically added to the medium in the tank and furthermore, ammonia water was aseptically added thereto to adjust pH of the culture solution to 6.8.

To this culture tank were aseptically added 150 ml of methanol and 200 ml of the above seed liquor and thereto ammonia water was further added at 30° C. to maintain pH of culture broth at 6.8 with stirring with an aeration of 10 l/min and at 300 rpm. With growth of microorganism, concentration of methanol in culture broth decreased. This was detected by analyzing methanol in exhaust gas by gas chromatography and methanol in an amount corresponding to this decrease was supplied to maintain the concentration of methanol in culture solution at 0.1–0.5 % by weight.

In this way, culturing was conducted in two culture tanks of 30 l in capacity for 10 days and pH of the culture broth in the culture tank was adjusted to 4.0 and then thereto were added (1) 120 g of L-serine/15 l and (2) 120 g of D-serine/15 l, respectively. Reaction was allowed to proceed for 24 hours at 30° C. with stirring under aeration and adjusting pH of culture broth to 4.0 to obtain reaction mixtures. After adjusting pH of the reaction mixture to 7.0, and the reaction mixture was subjected to centrifugation to obtain supernatant liquid.

Contents of hydroxymethyl OPQ in the reaction supernatant liquid are shown in Table 11.

TABLE 11

| Experiment No. | Content of hydroxymethyl OPQ (mg/l supernatant liquid) |
|---|---|
| (1) | 140 |
| (2) | 137 |

Example 14

Culturing was carried out for 10 days using culture tank of 30 liters in the same manner as in Example 13 except that *Hyphomicrobium methylovorum* DSM 1869 was used as strain and then, pH of culture broth was adjusted to 4.0 and 42 g of L-serine was added thereto and reaction was allowed to proceed.

After addition of L-serine, reaction mixture was taken every time, adjusted to pH 7 and subjected to Centrifugation and content of hydroxymethyl OPQ contained in the reaction mixture was measured.

The results are shown in Table 12.

TABLE 12

| Time elapsing after addition of L-serine | Content of hydroxymethyl OPQ (mg/l reaction mixture) |
|---|---|
| 1 hour | 35 |
| 2 hours | 109 |
| 4 hours | 177 |
| 10 hours | 240 |
| 14 hours | 262 |

Example 15

In the same manner as in Example 13, *Methylobacillus glycogenes* FERM P-2247 was cultured for 4 days in culture tanks of 30 liters.

Thereafter, pH of culture broth in the culture tank was adjusted to 4.5, 42 g of L-serine was added thereto and reaction was allowed to proceed for 6 hours to obtain a reaction mixture. After adjusting pH of the reaction mixture to 7.0, the reaction mixture was subjected to centrifugation to obtain supernatant liquid. Accumulation amount of hydroxymethyl OPQ in the supernatant liquid was 200 mg in 1 liter of the reaction mixture.

Example 16

*Paracoccus denitrificans* ATCC 19367 was cultured for 10 days in a culture tank of 30 liter in capacity in the same manner as in Example 13 except that strain was changed.

Then, culture broth in the culture tank was adjusted to pH 6.0, 42 g of D-serine was added thereto, and reaction was allowed to proceed for 6 hours to obtain a reaction mixture. Accumulation amount of hydroxymethyl OPQ was 110 mg in 1 liter of the reaction mixture.

Example 17

*Methylophaga thalassica* ATCC 33146 was cultured for 10 days in a culture tank of 30 liters in capacity in the same manner as in Example 13 except that strain was changed and sea water was used as water for medium.

Then, pH of the culture broth was adjusted to 4.0, 42 g of DL-serine was added thereto, and reaction was allowed to proceed for 6 hours at 30° C. with stirring under aeration to obtain a reaction mixture. After adjusting pH of the reaction mixture to 7.0, the reaction mixture was subjected to centrifugation to obtain supernatant liquid. Accumulation amount of hydroxymethyl OPQ in the supernatant liquid was 142 mg in 1 liter of the reaction mixture.

Example 18

In the same manner as in Example 14, *Hyphomicrobium methylovorum* DSM 1869 was cultured in a culture tank of 30 liters to obtain 15 l of culture broth. Each 200 ml of this culture broth was charged in a conical flask of 1 liter in capacity and each 0.6 g of various amino acids was added thereto. The culture broth was adjusted to pH 4.7 or 9 with NaOH or HCl and reaction was allowed to proceed at 30° C. for 24 hours under shaking to obtain reaction mixtures.

Reaction mixture in each flask was adjusted to pH 7.0 and then subjected to centrifugation to obtain supernatant liquid. Content of OPQs in the supernatant liquid is shown in Table 13.

TABLE 13

| No. | Amino acid added | Content of X-OPQ produced (mg/l) | | | X |
|---|---|---|---|---|---|
| | | Reaction pH 4 | Reaction pH 7 | Reaction pH 9 | |
| 1 | Glycine | 204 | 322 | 309 | (OPQ) |
| 2 | L-alanine | 144 | 185 | 167 | methyl |
| 3 | L-valine | 145 | 177 | 244 | 1-methylethyl |
| 4 | L-leucine | 150 | 239 | 243 | 2-methyl-propyl |
| 4 | L-isoleucine | 139 | 213 | 280 | 1-methyl-propyl |
| 6 | L-methionine | 101 | 131 | 138 | 2-methylthio-ethyl |
| 7 | L-glutamic acid | 142 | 222 | 217 | 2-carboxy-ethyl |
| 8 | L-glutamine | 232 | 305 | 303 | 2-carbamoyl-ethyl |
| 9 | L-phenyl-alanine | 201 | 379 | 319 | benzyl |
| 10 | L-aspartic acid | 79 | 147 | 113 | carboxy-methyl |
| 11 | L-asparagine | 14 | 220 | 215 | carbamoyl-methyl |
| 12 | L-arginine | 115 | 189 | 40 | 3-guanidino-propyl |
| 13 | L-histidine | 89 | 181 | 68 | 4-imidazolyl-methyl |
| 14 | L-lysine | 89 | 68 | 5 | 4-amino butyl |

X-OPQ: OPQs corresponding to respective amino acids.

Example 19

Each 200 ml of the same culture broth as the PQQ containing culture broth used in Example 18 was charged in twelve conical flasks of 1 liter in capacity, respectively.

Each 0.6 g of L-threonine, L-tyrosine, L-serine or L-cystine was added to each flask and pH of the culture broth was adjusted to 4, 7 or 9 with NaOH or HCl and reaction was allowed to proceed at 30° C. for 24 hours under shaking to obtain reaction mixtures.

Reaction mixture in each flask was adjusted to pH 7.0 and subjected to centrifugation to obtain supernatant liquid. Content of OPQs in the supernatant liquid is shown in Table 14.

OPQ was present in each reaction mixture in addition to OPQs corresponding to respective amino acids.

TABLE 14

| No. | Amino acid added | Reaction pH | OPQs produced (mg/l) | | X |
|---|---|---|---|---|---|
| | | | OPQ | X-OPQ | |
| 1 | L-threonine | 4 | 115 | 34 | Hydoxyethyl |
| 2 | L-threonine | 7 | 291 | 13 | |
| 3 | L-threonine | 9 | 311 | 3 | |
| 4 | L-tyrosine | 4 | 11 | 91 | 4-Hydroxy-phenylmethyl |
| 5 | L-tyrosine | 7 | 45 | 209 | |
| 6 | L-tyrosine | 9 | 157 | 59 | |
| 7 | L-serine | 4 | 13 | 182 | Hydroxymethyl |
| 8 | L-serine | 7 | 262 | 66 | |
| 9 | L-serine | 9 | 309 | 10 | |
| 10 | L-cystine | 4 | 5 | 5 | Mercapto-methyl |
| 11 | L-cystine | 7 | 45 | 58 | |

TABLE 14-continued

| No. | Amino acid added | Reaction pH | OPQs produced (mg/l) OPQ | X-OPQ X |
|---|---|---|---|---|
| 12 | L-cystine | 9 | 26 | 10 |

X-OPQ: OPQs corresponding to respective amino acids.

Example 20

The reaction mixture obtained in the same manner as Example 9 at 30° C. was subjected to centrifugation at 12,000 G for 20 min. to obtain supernatant liquid.

Fifty ml each of the supernatant luquid was controlled to pH 7.2, 6.5, 5.7, 5.0, 4.7, 4.2, 3.7, 3.1, 2.6, 2.1, 1.5 and 1.0, respectively, with HCl, and then was left to stand for 4 hrs under room temperature followed by centrifugation (12000 G, 20 min.). OPQ was precipitated and recovered.

OPQ left unrecovered in the supernatant liquid were assayed by high performance liquid chromatography. The results are shown in Table 15. OPQ was recovered in the form of precipitate when pH was 4 or less.

TABLE 15

| pH | OPQ in the supernatant liquid (mg/l reaction mixture) |
|---|---|
| 7.2 | 284 |
| 6.5 | 285 |
| 5.7 | 272 |
| 5.0 | 288 |
| 4.7 | 269 |
| 4.2 | 191 |
| 3.7 | 66 |
| 3.1 | 24 |
| 2.6 | 14 |
| 2.1 | 7 |
| 1.5 | 12 |
| 1.0 | 15 |

Example 21

30.0 g of L-serine was dissolved in 600 ml of distilled water and the solution was adjusted to pH 3.0 with 6N hydrochloric acid to obtain an L-serine solution. To this L-serine solution was added 04 mg of PQQ and reaction was allowed to proceed at 30° C. for 20 hours under vigorous mechanical stirring with aeration. As a result, concentration of hydroxymethyl OPQ in the reaction mixture was about 890 mg/l.

This reaction mixture was adjusted to pH 2.0 with 6N hydrochloric acid and 12 g of $CaCl_2.2H_2O$ was added thereto and this liquid was cooled with ice water to precipitate hydroxymethyl OPQ.

This precipitate was recovered by centrifugal separation. To this precipitate was added 600 ml of water and this liquid was adjusted to pH 7.8 with 5N NaOH to dissolve the precipitate.

To the resulting solution is added 100 ml of DEAE-SEPHADEX A-25 which was an anion exchange carrier and the mixture was well stirred to adsorb hydroxymethyl OPQ onto the carrier and was left to stand. Supernatant liquid was removed and the carrier was separated and recovered.

100 ml of fresh DEAE-SEPHADEX A-25 was charged in a column of 50 mm$\phi$ and the recovered carrier was charged thereover.

Through this column were passed 300 ml of distilled water, then 3400 ml of 0.5M aqueous sodium chloride solution and subsequently 2500 ml of 0.7M aqueous sodium chloride solution. At this time, a slight amount of unreacted PQQ entrained by hydroxymethyl OPQ was present in fraction of 0.5M aqueous sodium chloride solution and hydroxymethyl OPQ was present in fraction of 0.7M aqueous sodium chloride solution.

The fraction of 0.7M aqueous sodium chloride solution was adjusted to pH 2.0 with 6N hydrochloric acid and then cooled to 5° C. to precipitate hydroxymethyl OPQ.

The resulting precipitate was recovered by centrifugal separation and washed with dilute hydrochloric acid and then with diethyl ether and thereafter dried at about 60° C. in vacuo to obtain 330 mg of hydroxymethyl OPQ.

The thus obtained hydroxymethyl OPQ had orange color and gradually decomposed at 210°–220° C. and did not show clear melting point. This hydroxymethyl OPQ was easily soluble in water and very easily soluble under neutral and alkaline conditions and furthermore, dissolved in lower alcohols, but did not dissolve in acetone and diethyl ether.

Color of aqueous solution of the hydroxymethyl OPQ differed depending on concentration of hydroxymethyl OPQ and pH of the aqueous solution and aqueous hydroxymethyl OPQ solution of about 10 mg/l was light yellow under neutral to alkaline condition and was reddish light yellow under acidic condition.

Elemental analysis value, IR spectrum, $^1$H-NMR spectrum, and visible.ultraviolet spectrum of the above hydroxymethyl OPQ are shown below.

(1) Elemental analysis value: $C_{16}H_9N_3O_8$ (MW 371.25) Calcd. (%): C 51.76 H 2.44 N 11.32 Found (%): C 50.58 H 2.63 N 11.08

(2) IR spectrum (Vmax, cm$^{-1}$): (KBr) $2500^{br,s}$, $1680^{sh,w}$, $1575^{sh,s}$, $1510^s$, $1150^{vs}$, $1095^{sh,s}$, $700^m$, $650^m$ (3) $^1$H-NMR spectrum ($\delta$ value, ppm): (DMSO-d$_6$, internal standard: TMS) 4.98 (s,2H,CH$_2$-OH), 7.27 (D,1H, pyrrole ring C-H,J=1.98Hz), 8.07 (s,1H, pyridine ring C-H), 14.60 (d, 1H, pyrrole ring N-H, J=0.44Hz)

(4) Visible ultraviolet spectrum ($\lambda_{max}$.nm): (10 mM potassium phosphate buffer pH 7.0) 254, 269$^{sh}$, 416

Example 22

40 ml each of aqueous L-serine solution of 10 g/l adjusted to pH 1.5–9 with hydrochloric acid or sodium hydroxide was charged in a conical flask each of ml in capacity and 40 mg each of PQQ was added to respective conical flask.

A gas permeable stopper was placed on each conical flask and content of the flask was stirred using a rotary shaker to allow reaction to proceed for one day at 30° C.

The reaction mixture was adjusted to pH 8.0 and amount of hydroxymethyl OPQ produced was determined by a high performance liquid chromatography.

Conditions of high performance liquid chromatography are shown below.

Measuring device: Manufactured by Shimadzu Seisakusho Ltd. Pump LC-6A Detector SPD-6AV Column thermostat CTO-6AS ( 40 ° C.)

Column : Manufactured by YMC Co. ODS A-302 4.6 mm$\phi \times$150 mm

Measuring wavelength: 259 nm

Flow rate : 1.5 ml/min

Composition of eluent: 0.1M $KH_2PO_4$, 0.1M $HClO_4$ 10% aqueous $CH_3CN$ solution 10 pH 2.5 (NaOH)

The results are shown in Table 16.

TABLE 16

| pH of reaction solution | Concentration of hydroxy-methyl OPQ (mg/l) |
| --- | --- |
| 1.5 | 153 |
| 2.0 | 580 |
| 3.0 | 806 |
| 4.0 | 791 |
| 5.0 | 671 |
| 7.0 | 245 |
| 8.0 | 162 |
| 9.0 | 60 |

Example 23

7.8 g of L-valine was dissolved in 200 ml of distilled water and the solution was adjusted to pH 8.5 with 5N NaOH. Thereto was added 801 mg of PQQ . disodium salt and reaction was allowed to proceed at 30° C. for 21 hours under vigorous mechanical stirring with aeration. This reaction mixture was adjusted to pH 1.6 with 6N hydrochloric acid and was cooled to 5° C. to precipitate 1-methylethyl OPQ.

This precipitate was recovered by centrifugal separation and to this precipitate was added 200 ml of water and this liquid was adjusted to pH 8.7 with 5N NaOH to dissolve the precipitate.

To the resulting solution was added 50 ml of DEAE-SEPHADEX A-25 which was an anion exchange carrier and the mixture was well stirred to adsorb 1-methylethyl OPQ to the carrier and was left to stand. Supernatant liquid was removed and the carrier was separated and recovered.

75 ml of fresh DEAE-SEPHADEX A-25 was charged in a column of 50 mm$\phi$ and the recovered carrier was charged thereover.

Through this column were passed 300 ml of distilled water to wash the content, then 3700 ml of 0.4M aqueous sodium chloride solution and subsequently 4300 ml of 0.6M aqueous sodium chloride solution. At this time, 1-methylethyl OPQ contained in the reaction mixture was mainly present in fraction of 0.6M aqueous sodium chloride solution.

The fractions of 0.4M aqueous sodium chloride solution and 0.6M aqueous sodium chloride solution in which 1-methylethyl OPQ was eluted were adjusted to pH 1.7 with 6N hydrochloric acid. Then n-butanol was added thereto and the mixture was left to stand. Then, n-butanol layer containing 1-methylethyl OPQ was separated and recovered. The n-butanol layer was mixed with 0.1N hydrochloric acid and washed and the n-butanol layer was separated, recovered and concentrated to dryness. Thereto was added diethyl ether and the resulting precipitate was filtrated and recovered. The precipitate was dried at about 70° C. in vacuo to obtain 460 mg of 1-methylethyl OPQ.

The thus obtained 1-methylethyl OPQ had orange color and gradually decomposed at 255°–259° C. and did not show clear melting point. This 1-methylethyl OPQ was easily soluble in water and very easily soluble under neutral and alkaline conditions and it also dissolved in lower alcohols, but did not dissolve in acetone and diethyl ether.

Color of aqueous solution of the 1-methylethyl OPQ differed depending on concentration of 1-methylethyl OPQ and pH of the aqueous solution and aqueous 1-methylethyl OPQ solution of about 10 mg/l was light yellow under pH of neutral to alkaline condition and was reddish light yellow under acidic condition.

Elemental analysis value, IR spectrum, $^1$H-NMR spectrum, and visible . ultraviolet spectrum of the resulting 1-methylethyl OPQ are shown below.

(1) Elemental analysis value: $C_{18}H_{13}N_3O_7.H_2O$ (MW 401.33) Calcd. (%): C 53.87 H 3.77 N 10.47 Found (%): C 53.61 H 3.96 N 10.22

(2) IR spectrum ($V_{max}$, cm$^{-1}$): (KBr) 2850$^{br,s}$, 2530$^{sh,s}$, 1575$^s$, 1515$^{sh,m}$, 1175$^{vs}$, 1100$^{sh,m}$, 1015$^{sh,m}$, 815$^{sh,w}$755$^m$, 730$^m$, 660$^{sh,w}$ (3) $^1$H-NMR spectrum ($\delta$ value, ppm): (DMSO-d$_6$, internal standard: TMS) 1.36(d,6H,C$\underline{H}$-(CH$_3$), J=6.4Hz), 3.74 (hep, 1H, C$\underline{H}$-(CH$_3$)$_2$, J=6.7Hz ), 7.29 (d, 1H, pyrrole ring C-$\underline{H}$, J=1.8Hz), 8.00(s,1H, pyridine ring C-$\underline{H}$), 13.01(brs, 1H, pyrrole ring N-$\underline{H}$)

(4) Visible-ultraviolet spectrum ($\lambda_{max}$,nm): (10 mM potassium phosphate buffer pH 7.0) 255, 272$^{sh}$, 418

Example 24

5.1 g of L-isoleucine was dissolved in 0 ml of distilled water and the solution was adjusted to pH 8.5 with 5N NaOH. To this L-isoleucine solution was added 805 mg of PQQ-disodium salt and reaction was allowed to proceed at 30° C. for 21 hours under vigorous mechanical stirring with aeration. This reaction mixture was adjusted to pH 1.8 with 6N hydrochloric acid and was cooled to 5° C. to precipitate 1-methylpropyl OPQ.

This precipitate was recovered by centrifugal separation and to this precipitate was added 200 ml of water and this liquid was adjusted to pH 8.2 with 5N NaOH to dissolve the precipitate.

To the resulting solution was added 50 ml of DEAE-SEPHADEX A-25 which is an anion exchange carrier and the mixture was well stirred to adsorb 1-methylpropyl OPQ to the carrier and was left to stand. Supernatant liquid was removed and the carrier was separated and recovered.

75 ml of fresh DEAE-SEPHADEX A-25 was charged in a column of 50 mm$\phi$ and the recovered carrier was charged thereover.

Through this column were passed 700 ml of distilled water to wash the content, then 3800 ml of 0.5M aqueous sodium chloride solution and subsequently 1800 ml of 0.8M aqueous sodium chloride solution. At this time, 1-methylpropyl OPQ contained in the reaction mixture was mainly present in fraction of 0.5M aqueous sodium chloride solution.

The fractions of 0.5M aqueous sodium chloride solution and 0.8M aqueous sodium chloride solution in which 1-methylpropyl OPQ was eluted were adjusted to pH 1.9 with 6N hydrochloric acid. Then n-butanol was added thereto and the mixture was left to stand. Then, n-butanol layer containing 1-methylpropyl OPQ was separated and recovered. Further, this n-butanol layer was mixed with 0.1N hydrochloric acid and washed and then, the n-butanol layer was separated and recovered and concentrated to dryness. Thereto was added diethyl ether and the resulting precipitate was filtrated. The precipitate was dried at about 70° C. in vacuo to obtain 410 mg of 1-methylpropyl OPQ.

The thus obtained 1-methylpropyl OPQ had orange color and gradually decomposed at 250°–254° C. and did not show clear melting point. This 1-methylpropyl OPQ was easily soluble in water and very easily soluble under neutral and alkaline conditions and it also dissolved in lower alcohols, but did not dissolve in acetone and diethyl ether.

Color of aqueous solution of the 1-methylpropyl OPQ differed depending on concentration of 1-methylpropyl OPQ and pH of the aqueous solution and aqueous 1-methylpropyl OPQ solution of about 10 mg/l was light yellow under pH of neutral to alkaline condition and was reddish light yellow under acidic condition.

Elemental analysis value, IR spectrum, $^1$H-NMR spectrum, and visible-ultraviolet spectrum of the above methylpropyl OPQ are shown below.

(1) Elemental analysis value: $C_{19}H_{15}N_3O_7 \cdot H_2O$ (MW 415.36) Calcd. (%): C 54.94 H 4.13 N 10.12 Found (%): C 54.68 H 4.20 N 9.88

(2) IR spectrum ($\lambda_{max}$, cm$^{-1}$): (KBr) 2900$^{br,s}$, 2530$^{sh,s}$, 1605$^s$, 1520$^{sh,m}$, 1180$^{vs}$, 1145$^{sh,m}$, 1100$^{sh,m}$, 850$^w$, 760$^m$, 725$^{sh,m}$, 670$^{sh,w}$ (3) $^1$H-NMR spectrum ($\delta$ value, ppm): (DMSO-d$_6$, internal standard TMS) 0.83(t,3H, CH(CH$_3$)-CH$_2$-CH$_3$, J=7.3Hz), 1.38(d,3H, CH(CH$_3$)-CH$_2$-CH$_3$, J=6.8Hz) 1.71(m,2H, CH(CH$_3$)-CH$_2$-CH$_3$), 3.54 (hex,1H,CH(CH$_3$)-CH$_2$-CH$_3$, J=6.5Hz), 7.31 (d,1H, pyrrole ring C-H,J=2.4Hz), 7.98 (s, 1H, pyridine ring C-H), 13.07 (brs, 1H, pyrrole ring N-H)

(4) Visible ultraviolet spectrum ($\lambda_{max}$, nm): (10 mM potassium phosphate buffer pH 7.0) 256, 272$^{sh}$, 418

Example 25

3.2 g of L-leucine was dissolved in 200 ml of distilled water and the solution was adjusted to pH 8.5 with 5N NaOH. To this L-leucine solution was added 802 mg of PQQ.disodium salt and reaction was allowed to proceed at 30° C. for 21 hours under vigorous mechanical stirring with aeration. This reaction mixture was adjusted to pH 1.7 with 6N hydrochloric acid and was cooled to 5° C. to precipitate 2-methylpropyl OPQ.

This precipitate was recovered by centrifugal separation and to this precipitate was added 200 ml of water and this liquid was adjusted to pH 8.3 with 5N NaOH to dissolve the precipitate.

To the resulting solution is added 50 ml of DEAE-SEPHADEX A-25 which is an anion exchange carrier and the mixture was well stirred to adsorb 2-methylpropyl OPQ to the carrier and was left to stand. Supernatant liquid was removed and the carrier was separated and recovered.

50 ml of fresh DEAE-SEPHADEX A-25 was charged in a column of 50 mm$\phi$ and the recovered carrier was charged thereover.

Through this column were passed 300 ml of distilled water to wash the content, then 2000 ml of 0.5M aqueous sodium chloride solution and subsequently 2000 ml of 0.8M aqueous sodium chloride solution and then 500 ml of 2M aqueous sodium chloride solution. At this time, 2-methylpropyl OPQ contained in the reaction mixture was mainly present in fraction of 0.8M aqueous sodium chloride solution.

The fraction of 0.8M aqueous sodium chloride solution in which 2-methylpropyl OPQ was eluted were adjusted to pH 1.8 with 6N hydrochloric acid and methylpropyl OPQ was precipitated at 5° C. The resulting precipitate was recovered by centrifugal separation, washed with 0.1N hydrochloric acid and then dried at about 70° C. in vacuo to obtain 430 mg of 2-methylpropyl OPQ.

The thus obtained 2-methylpropyl OPQ had orange color and gradually decomposed at 248°–252° C. and did not show clear melting point. This 2-methylpropyl OPQ was easily soluble in water and very easily soluble under neutral and alkaline conditions and it also dissolved in lower alcohols, but did not dissolve in acetone and diethyl ether.

Color of aqueous solution of the 2-methylpropyl OPQ differed depending on concentration of 2-methylpropyl OPQ and pH of the aqueous solution and aqueous 2-methylpropyl OPQ solution of about 10 mg/l was light yellow under pH of neutral to alkaline condition and was reddish light yellow under acidic condition.

Elemental analysis value, IR spectrum, $^1$H-NMR spectrum, and visible-ultraviolet spectrum of the above 2-methylpropyl OPQ are shown below.

(1) Elemental analysis value: $C_{19}H_{15}N_3O_7 \cdot H_2O$ (MW 415.36) Calcd.. (%): C 54.94 H 4.13 N 10.12 Found (%): C 54.70 H 4.27 N 9.85

(2) IR spectrum ($\lambda_{max}$, cm$^{-1}$): (KBr) 2880$^{br,s}$, 2520$^{sh,s}$, 2330$^{sh,m}$, 1585$^s$,1520$^{sh,m}$, 1180$^{vs}$, 760$^{sh,m}$, 735$^m$, 670$^{sh,w}$.

(3) $^1$H-NMR spectrum ($\delta$ value, ppm): (DMSO-d$_6$, internal standard: TMS) 0.93 (d,6H,CH$_2$-CH-(CH$_3$)$_2$, J=6.6Hz), 2.16 (m, 1H, CH$_2$-CH-(CH$_3$)$_2$), 3.08 (d,2H,CH$_2$-CH-(CH$_3$)$_2$,J=7.0Hz), 7.28 (d, 1H, pyrrole ring C-H, J=2.2Hz), 7.99 (s, 1H, pyridine ring C-H,), 12.60 (brs, 1H, pyrrole ring N-H,)

(4) Visible ultraviolet spectrum ($\lambda_{max}$, nm): (10 mM potassium phosphate buffer pH 7.0) 255, 272$^{sh}$, 419

Example 26

4.3 g of L-alanine was dissolved in 800 ml of distilled water and the solution was adjusted to pH 4.0 with in hydrochloric acid.

To this L-alanine solution was added 800 mg of PQQ and reaction was allowed to proceed at 30° C. for 30 hours under vigorous mechanical stirring with aeration. To this reaction mixture was added 23.4 g of sodium chloride and the mixture was adjusted to pH 1.6 with 6N hydrochloric acid and was cooled to 5° C. to precipitate methyl OPQ.

This precipitate was recovered by centrifugal separation and to this precipitate was added 250 ml of distilled water and this liquid was adjusted to pH 7.4 with 5N NaOH to dissolve the precipitate.

To the resulting solution was added 50 ml of DEAE-SEPHADEX A-25 which is an anion exchange carrier and the mixture was well stirred to adsorb methyl OPQ to the carrier and was left to stand. Supernatant liquid was removed and the carrier was separated and recovered.

75 ml of fresh DEAE-SEPHADEX A-25 was charged in a column of 50 mm$\phi$ and the recovered carrier was charged thereover.

Through this column were passed 400 ml of distilled water to wash the content and then 6900 ml of 0.5M aqueous sodium chloride solution. At this time, methyl OPQ contained in the reaction mixture was present in fraction of 0.5M aqueous sodium chloride solution.

The obtained fraction in which methyl OPQ was eluted was adjusted to pH 1.0 with 6N hydrochloric acid and methyl OPQ was precipitated at 5° C. The resulting precipitate was recovered by centrifugal separation and washed with 0.1N hydrochloric acid and was dried at about 70° C. in vacuo to obtain 273 mg of methyl OPQ.

The thus obtained methyl OPQ had orange color and gradually decomposed at 262°–268° C. and did not show clear melting point. This was easily soluble in water and very easily soluble under neutral and alkaline conditions and it also dissolved in lower alcohols, but did not dissolve in acetone and diethyl ether.

Color of aqueous solution of the methyl OPQ differed depending on concentration of methyl OPQ and pH of the aqueous solution and aqueous methyl OPQ solution of about 10 mg/l was light yellow under pH of neutral to alkaline condition and was reddish light yellow under acidic condition.

Elemental analysis value, IR spectrum, $^1$H-NMR spectrum, and visible-ultraviolet spectrum of the above methyl OPQ are shown below.

(1) Elemental analysis value: $C_{16}H_9N_3O_7 \cdot H_2O$ (MW 373.28) Calcd. (%): C 51.48 H 2.97 N 11.26 Found (%): C 51.20 H 3.24 N 11.03

(2) IR spectrum ($\lambda_{max}$, cm$^{-1}$): (KBr) $2725^{br,s}$, $2480^{br,s}$, $1590^s$, $1515^2$, $1170^{vs}$, $1095^{sh,s}$, $965^m$, $750^m$, $710^m$.

(3) $^1$H-NMR spectrum ($\delta$ value, ppm): (DMSO-d$_6$, internal standard: TMS) 273(s,3H,C$\underline{H}_3$), 7.18(d,1H, pyrrole ring C-$\underline{H}$), 7.92(s,1H, pyridine ring C-$\underline{H}$), 12.82(brs,1H, pyrrole ring N-$\underline{H}$)

(4) Visible-ultraviolet spectrum ($\lambda_{max}$, nm): (10 mM potassium phosphate buffer pH 7.0) 255, 272, 418

Example 27

6.4 g of L-glutamic acid was dissolved in 800 ml of distilled water and the solution was adjusted to pH 4.0 with 5N NaOH.

To this L-glutamic acid solution was added 800 mg of PQQ and reaction was allowed to proceed at 30° C. for 26 hours under vigorous mechanical stirring with aeration. This reaction mixture was adjusted to pH 1.0 with 6N hydrochloric acid and was mixed with n-butanol and the mixture was left to stand to separate and recover n-butanol layer containing 2-carboxyethyl OPQ. Furthermore, to this n-butanol layer was added 0.1N NaOH and they were mixed. The mixture was left to stand to separate and recover aqueous layer containing 2-carboxyethyl OPQ. This liquid was adjusted to pH 8.0 with 6N hydrochloric acid and distilled water was added to make up 450 ml.

To the resulting solution was added 50 ml of DEAE-SEPHADEX A-25 which is an anion exchange carrier and the mixture was well stirred to adsorb 2-carboxyethyl OPQ to the carrier and was left to stand. Supernatant liquid was removed and the carrier was separated and recovered.

75 ml of fresh DEAE-SEPHADEX A-25 was charged in a column of 50 mm$\phi$ and the recovered carrier was charged thereover.

Through this column were passed 400 ml of distilled water to wash the content, then 3400 ml of 0.4M aqueous sodium chloride solution and subsequently 3800 ml of 0.6M aqueous sodium chloride solution. At this time, 2-carboxyethyl OPQ contained in the reaction mixture was present in fraction of 0.6M aqueous sodium chloride solution.

This fraction in which 2-carboxyethyl OPQ was eluted was adjusted to pH 0.9 with 6N hydrochloric acid and 2-carboxyethyl OPQ was precipitated at 5° C. The resulting precipitate was recovered by centrifugal separation, washed with 0.1N hydrochloric acid and then dried at about 70° C. in vacuo to obtain 358 mg of 2-carboxyethyl OPQ.

The thus obtained 2-carboxyethyl OPQ had orange color and gradually decomposed at 266°–271° C. and did not show clear melting point. This was easily soluble in water and very easily soluble in water under neutral and alkaline conditions and it also dissolved in lower alcohols, but did not dissolve in acetone and diethyl ether.

Color of aqueous solution of the 2-carboxyethyl OPQ differed depending on concentration of 2-carboxyethyl OPQ and pH of the aqueous solution and aqueous 2-carboxyethyl OPQ solution of about 10 mg/l was light yellow under pH of neutral to alkaline condition and was reddish light yellow under acidic condition.

Elemental analysis value, IR spectrum, $^1$H-NMR spectrum, and visible-ultraviolet spectrum of the above 2-carboxyethyl OPQ are shown below.

(1) Elemental analysis value: $C_{18}H_{11}N_3O_9 \cdot H_2O$ (MW 431.31) Calcd. (%): C 50.12 H 3.04 N 9.74 Found (%): C 49.85 H 3.33 N 9.62

(2) IR spectrum ($\lambda_{max}$, cm$^{-1}$): (KBr) $2840^{br,s}$, $2500^m$, $2340^{sh,m}$, $1570^s$, $1515^s$, $1175^{vs}$, $1100^{sh,m}$, $755^w$, $730^w$, (3) $^1$H-NMR spectrum ($\delta$ value, ppm): (DMSO-d$_6$, internal standard: TMS) 2.85(t,2H,C$\underline{H}_2$-CH$_2$-CO$_2$H,J=6.2Hz), 3.30 (t,2H, C$\underline{H}_2$-CH$_2$-CO$_2$H, J=5.9Hz), 7.23 (brs, 1H, pyrrole ring C-H), 7.98 (s, 1H, pyridine ring C-H), 13.67 (brs, 1H, pyrrole ring N-$\underline{H}$)

(4) Visible-ultraviolet spectrum ($\lambda_{max}$,nm): (10 mM potassium phosphate buffer pH 7.0) 256, 275$^{sh}$, 419

Example 28

6.4 g of L-glutamine was dissolved in 800 ml of distilled water and the solution was adjusted to pH 4.0 with 1N hydrochloric acid.

To this L-glutamine solution was added 800 mg of PQQ and reaction was allowed to proceed at 30° C. for 30 hours under vigorous mechanical stirring with aeration. To this reaction mixture was added 23.4 g of sodium chloride to dissolve it therein and then was adjusted to pH 2.0 with 6N hydrochloric acid. This was cooled to 5° C. to precipitate 2-carbamoylethyl OPQ.

This precipitate was recovered by centrifugal separation and to this precipitate was added 250 ml of distilled water and this liquid was adjusted to pH 7.2 with 5N NaOH to dissolve the precipitate.

To the resulting solution was added 50 ml of DEAE-SEPHADEX A-25 which is an anion exchange carrier and the mixture was well stirred to adsorb 2-carbamoylethyl OPQ to the carrier and was left to stand. Supernatant liquid was removed and the carrier was separated and recovered.

75 ml of fresh DEAE-SEPHADEX A-25 was charged in a column of 50 mm$\phi$ and the recovered carrier was charged thereover.

Through this column were passed 400 ml of distilled water to wash the content, then 5800 ml of 0.4M aqueous sodium chloride solution, and then 1100 ml of 0.6M aqueous sodium chloride solution. At this time, nearly the whole amount of 2-carbamoylethyl OPQ contained in the reaction mixture was present in the fraction of 0.6M aqueous sodium chloride solution.

The fractions of 0.4M aqueous sodium chloride solution and 0.6M aqueous sodium chloride solution in which 2-carbamoylethyl OPQ was eluted were adjusted to pH 1.8 with 6N hydrochloric acid and 2-carbamoylethyl OPQ was precipitated at 5° C. The resulting precipitate was recovered by centrifugal separation, washed with 0.1N hydrochloric acid and dried at about 70° C. in vacuo to obtain 373 mg of 2-carbamoylethyl OPQ.

The thus obtained 2-carbamoylethyl OPQ had orange color and gradually decomposed at 286°–290° C. and did not show clear melting point. This was easily soluble in water and very easily soluble in water under neutral and alkaline conditions and it also dissolved in lower alcohols, but did not dissolve in acetone and diethyl ether.

Color of aqueous solution of the 2-carbamoylethyl OPQ differed depending on concentration of 2-carbamoylethyl OPQ and pH of the aqueous solution and aqueous 2-carbamoylethyl OPQ solution of about mg/l was light yellow under pH of neutral to alkaline condition and was reddish light yellow under acidic condition.

Elemental analysis value, IR spectrum, $^1$H-NMR spectrum, and visible.ultraviolet spectrum of the above 2-carbamoylethyl OPQ are shown below.

(1) Elemental analysis value: $C_{18}H_{12}N_4O_8 \cdot H_2O$ (MW 430.33) Calcd. (%): C 50.24 H 3.28 N 13.02 Found (%): C 50.01 H 3.50 N 12.87

(2) IR spectrum ($\lambda_{max}$, cm$^{-1}$): (KBr) 2735$^{br,m}$, 2500$^{br,m}$, 2300$^{sh,m}$, 1555$^{br,s}$, 1390$^S$, 1180$^{vs}$, 1100$^{sh,s}$, 990$^m$, 765$^m$, 560$^w$ (3) $^1$H-NMR spectrum (δ value, ppm): (DMSO-d$_6$, internal standard: TMS) 2.76(t,2H,CH$_2$-CH$_2$-CO-NH$_2$, J=6.7Hz), 3.31(t,2H,CH$_2$-CH$_2$-CO-NH$_2$,J=6.9Hz) 6.79 (brs, 1H, CH$_2$-CH$_2$CO-NH$_2$), 7.25 (d, 1H, pyrrole ring C-H,J=2.0Hz), 7.38 (brs, 1H, CH$_2$-CH$_2$-CO-NH$_2$), 7.97 (s, 1H, pyridine ring C-H), 12.91 (brs, 1H, pyrrole ring N-H)

(4) Visible-ultraviolet spectrum ($\lambda_{max}$,nm): (10 mM potassium phosphate buffer pH 7.0) 255, 272$^{sh}$, 418

Example 29

7.2 g of L-methionine was dissolved in 400 ml of distilled water and the solution was adjusted to pH 4.0 with 6N hydrochloric acid.

To this L-methionine solution was added 800 mg of PQQ and reaction was allowed to proceed at 30° C. for 26 hours under vigorous mechanical stirring with aeration. This reaction mixture was adjusted to pH 1.5 with 6N hydrochloric acid and was cooled to 5° C. to precipitate 2-methylthioethyl OPQ.

This precipitate was recovered by centrifugal separation and to this precipitate was added 250 ml of distilled water and this liquid was adjusted to pH 8.1 with 5N NaOH to dissolve the precipitate.

To the resulting solution was added 50 ml of DEAE-SEPHADEX A-25 which is an anion exchange carrier and the mixture is well stirred to adsorb 2-methylthioethyl OPQ to the carrier and was left to stand. Supernatant liquid was removed and the carrier was separated and recovered.

75 ml of fresh DEAE-SEPHADEX A-25 was charged in a column of 50 mmφ and the recovered carrier was charged thereover.

Through this column were passed 200 ml of distilled water to wash the content, then 4800 ml of 0.4M aqueous sodium chloride solution and subsequently 3000 ml of 0.5M aqueous sodium chloride solution and then 2000 ml of 0.6M aqueous sodium chloride solution.

At this time, most of 2-methylthioethyl OPQ contained in the reaction mixture was present in fraction of 0.5M aqueous sodium chloride solution.

The fractions of 0.5M aqueous sodium chloride solution and 0.6M aqueous sodium chloride solution in which 2-methylthioethyl OPQ was eluted were adjusted to pH 1.3 with 6N hydrochloric acid and then 2-methylthioethyl OPQ was precipitated at 5° C. The precipitate was recovered by centrifugal separation, washed with 0.1N hydrochloric acid and dried at about 70° C. in vacuo to obtain 470 mg of 2-methylthioethyl OPQ.

The thus obtained 2-methylthioethyl OPQ had orange color and gradually decomposed at 250°–258° C. and did not show clear melting point. This was easily soluble in water, especially soluble under neutral and alkaline conditions and it also dissolved in lower alcohols, but did not dissolve in acetone and diethyl ether.

Color of aqueous solution of the 2-methylthioethyl OPQ differed depending on concentration of 2-methylthioethyl OPQ and pH of the aqueous solution and aqueous 2-methylthioethyl OPQ solution of about 10 mg/l was light yellow under pH of neutral to alkaline condition and was reddish light yellow under acidic condition.

Elemental analysis value, IR spectrum, $^1$H-NMR spectrum, and visible ultraviolet spectrum of the above 2-methylthioethyl OPQ are shown below.

(1) Elemental analysis value: $C_{18}H_{13}N_3O_7S \cdot H_2O$ (MW 433.39) Calcd. (%): C 49.88 H 3.49 N 9.70 Found (%): C 49.63 H 3.77 N 9.49

(2) IR spectrum ($\lambda_{max}$, cm$^{-1}$): (KBr) 2775$^{br,s}$, 2500$^{br,m}$, 1575$^s$, 1510$^{sh,s}$, 1175$^{vs}$, 970$^w$, 850$^w$, 750$^m$, 720$^m$ (3) $^1$H-NMR spectrum (δ value, ppm): (DMSO-d$_6$, internal standard: TMS) 2.13(s,3H,CH$_2$-CH$_2$-S-CH$_3$), 2.98 (t, 2H, CH$_2$-CH$_2$-S-CH$_3$, J=7.7Hz), 3.45(t,2H,CH$_2$-CH$_2$-S-CH$_3$, J=7.9Hz), 7.23(d, 1H, pyrrole ring C-H,J=2.0Hz), 7.99(s, 1H, pyrridine ring C-H), 13.14 (brs,1H, pyrrole ring N-H,)

(4) Visible-ultraviolet spectrum ($\lambda_{max}$,nm): (10 mM potassium phosphate buffer pH 7.0) 256, 273$^{sh}$, 418

Example 30

8.0 g of L-phenylalanine was dissolved in ml of distilled water and the solution was adjusted to pH 4.0 with 6N hydrochloric acid.

To this L-phenylalanine solution was added 800 mg of PQQ and reaction was allowed to proceed at 30° C. for 26 hours under vigorous mechanical stirring with aeration. This reaction mixture was adjusted to pH 1.4 with 6N hydrochloric acid and was cooled to 5° C. to precipitate benzyl OPQ.

This precipitate was recovered by centrifugal separation and to this precipitate was added 250 ml of distilled water and this liquid was adjusted to pH 8.1 with 5N NaOH to dissolve the precipitate.

To the resulting solution was added 50 ml of DEAE-SEPHADEX A-25 which is an anion exchange carrier and the mixture was well stirred to adsorb benzyl OPQ to the carrier and was left to stand. Supernatant liquid was removed and the carrier was separated and recovered.

75 ml of fresh DEAE-SEPHADEX A-25 was charged in a column of 50 mmφ and the recovered carrier was charged thereover.

Through this column were passed 200 ml of distilled water to wash the content, then 5000 ml of 0.4M aqueous sodium chloride solution, subsequently 5000 ml of 0.5M aqueous sodium chloride solution and furthermore 5000 ml of 0.6M aqueous sodium chloride solution. At this time, benzyl OPQ contained in the reaction mixture was mainly present in fraction of 0.5M aqueous sodium chloride solution.

The fractions of 0.5M aqueous sodium chloride solution and 0.6M aqueous sodium chloride solution in which benzyl OPQ was eluted were adjusted to pH 1.2 with 6N hydrochloric acid and benzyl OPQ was precipitated at 5° C. The precipitate was recovered in centrifugal separation, washed with 0.1N hydrochloric acid and then dried at about 70° C. in vacuo to obtain 724 mg of benzyl OPQ.

The thus obtained benzyl OPQ had orange color and gradually decomposed at 244°–250° C. and did not show clear melting point. This was easily soluble in water, especially soluble under neutral and alkaline conditions and it also dissolved in lower alcohols, but did not dissolve in acetone and diethyl ether.

Color of aqueous solution of the benzyl OPQ differed depending on concentration of benzyl OPQ and pH of the aqueous solution and aqueous benzyl OPQ solution of about 10 mg/l was light yellow under pH of neutral to alkaline condition and was reddish light yellow under acidic condition.

Elemental analysis value, IR spectrum, $^1$H-NMR spectrum, and visible-ultraviolet spectrum of the above benzyl OPQ are shown below.
  (1) Elemental analysis value: $C_{22}H_{13}N_3O_7 \cdot H_2O$ (MW 449.37) Calcd. (%): C 58.80 H 3.36 N 9.35 Found (%): C 58.52 H 3.61 N 9.14
  (2) IR spectrum ($\lambda_{max}$, cm$^{-1}$): (KBr) 2710$^{br,s}$, 2490$^{br,s}$, 1575$^{br,s}$, 1490$^{sh,s}$, 1170$^{vs}$, 980$^w$, 710$^m$, 690$^m$, 660$^{sh,w}$
  (3) $^1$H-NMR spectrum (δ value, ppm): (DMSO-d$_6$, internal standard: TMS) 4.67(s,2H,C$\underline{H}_2$-C$_6$H$_5$), 7.02–7.90(m,6H, pyrrole ring C-$\underline{H}$,CH$_2$-C$_6\underline{H}_5$), 7.96 (s, 1H, pyridine ring C-$\underline{H}$), 12.95 (brs, pyrrole ring N-$\underline{H}$,)
  (4) Visible-ultraviolet spectrum ($\lambda_{max}$, nm): (10 mM potassium phosphate buffer pH 7.0) 256, 273$^{sh}$, 419

Example 31

4.4 g of L-tyrosine was dissolved in 400 ml of distilled water and the solution was adjusted to pH 4.0 with 1N hydrochloric acid.

To this L-tyrosine solution was added 800 mg of PQQ and reaction was allowed to proceed at 60° C. for 24 hours under vigorous mechanical stirring with aeration. This reaction mixture was cooled to 5° C. and precipitated L-tyrosine was filtered. The filtrate was adjusted to pH 1.0 with 6N hydrochloric acid and was cooled to 5° C. to precipitate 4-hydroxybenzyl OPQ.

This precipitate was recovered by centrifugal separation and to this precipitate was added 150 ml of distilled water and this liquid was adjusted to pH 7.3 with 5N NaOH to dissolve the precipitate.

To the resulting solution was added 50 ml of DEAE-SEPHADEX A-25 which is an anion exchange carrier and the mixture was well stirred to adsorb 4-hydroxybenzyl OPQ to the carrier and was left to stand. Supernatant liquid was removed and the carrier was separated and recovered.

75 ml of fresh DEAE-SEPHADEX A-25 was charged in a column of 50 mmφ and the recovered carrier was charged thereover.

Through this column were passed 500 ml of distilled water to wash the content, then 3700 ml of 0.4M aqueous sodium chloride solution and subsequently 6000 ml of 0.6M aqueous sodium chloride solution. At this time, 4-hydroxybenzyl OPQ adsorbed to the carrier was present in fraction of 0.6M aqueous sodium chloride solution.

This fraction in which 4-hydroxybenzyl OPQ was eluted was adjusted to pH 1.0 with 6N hydrochloric acid and 4-hydroxybenzyl OPQ was precipitated at 5° C. The precipitate was recovered by centrifugal separation and dissolved in methanol and the solution was concentrated to dryness. Thereto was added diethyl ether and the resulting precipitate was filtered. The precipitate was dried at about 70° C. in vacuo to obtain 357 mg of 4-hydroxybenzyl OPQ.

The thus obtained 4-hydroxybenzyl OPQ had reddish brown color and gradually decomposed at 263°–268° C. and did not show clear melting point. This was easily soluble in water, especially soluble under neutral and alkaline conditions and it also dissolved in lower alcohols, but did not dissolve in acetone and diethyl ether.

Color of aqueous solution of the 4-hydroxybenzyl OPQ differed depending on concentration of 4-hydroxybenzyl OPQ and pH of the aqueous solution and aqueous 4-hydroxybenzyl OPQ solution of about 10 mg/ml was light yellow under pH of neutral to alkaline condition and was reddish light yellow under acidic condition.

Elemental analysis value, IR spectrum, $^1$H-NMR spectrum, and visible-ultraviolet spectrum of the above 4-hydroxybenzyl OPQ are shown below.
  (1) Elemental analysis value: $C_{22}H_{13}N_3O_8 \cdot H_2O$ (MW 465.37) Calcd. (%): C 56.78 H 3.25 N 9.03 Found (%): C 56.51 H 3.52 N 8.87
  (2) IR spectrum ($\lambda_{max}$, cm$^{-1}$): (KBr) 2810$^s$, 2520$^{s,sh}$, 1590$^s$, 1500$^s$, 1415$^m$, 1180$^{vs}$, 990$^{w,sh}$, 820$^{w,sh}$, 760$^m$, 730$^m$, 670$^{w,sh}$
  (3) $^1$H-NMR spectrum (δ value, ppm): (DMSO-d$_6$, internal standard: TMS) 4.54 ( s, 2H, C$\underline{H}_2$-C$_6$H$_4$OH), 6.64 ( d, 2H, J=8.6Hz, CH$_2$ side benzene ring C-$\underline{H}$), 6.81(d,2H,J=8.1Hz, OH side benzene ring $\overline{\text{C-H}}$), 7.31(d,1H, pyrrole ring C-$\underline{H}$,J=2.0Hz), 7.94 (s, 1H, pyridine ring C-$\underline{H}$), 13.01 (brs, 1H, pyrrole ring N-$\underline{H}$)
  (4) Visible-ultraviolet spectrum ($\lambda_{max}$,nm): (10 mM potassium phosphate buffer pH 7.0) 256, 270$^{sh}$, 420

Example 32

Medulla of kidney of dog was homogenized with 10 mM phosphoric acid buffer (pH 7.0) containing 2 mM dithiothreitol in an amount of four times the volume of kidney medulla and subjected to centrifugation. The supernatant liquid was purified by affinity chromatography, gel filtration and chromatofocusing to obtain electrophoretically homogeneous aldose reductase.

0.05 ml of 3 mM NADPH, 0.1 ml of DL-glyceraldehyde and 0.04 ml of distilled water were added to 0.8 ml of 0.1M phosphoric acid buffer (pH 6.2) and left to stand at 25° C. for 3 minutes. Then, 0.01 ml of the aldose reductase solution was added thereto to start reaction and decreasing of absorbance of 340 nm was measured at 25° C. with time. Amount of enzyme which consumes 1 μmole of NADPH for 1 minute was taken as 1 unit.

Enzyme activity was measured under the same conditions as in the above measurement of aldose reductase activity except that 0.04 ml of aqueous solution of inhibitory substance in various concentrations was added in place of 0.04 ml of distilled water and degree of inhibition was calculated from comparison of the enzyme activity with the enzyme activity obtained in the absence of inhibitor. (1) OPQ, (2) methyl OPQ, (3) 1-methylpropyl OPQ, (4) 2-methylpropyl OPQ, (5) 2-carbamoylethyl OPQ, (6) hydroxymethyl OPQ, (7) 2-methylthioethyl OPQ, (8) 2-carboxyethyl OPQ, (9) 4-hydroxybenzyl OPQ, (10) 1-methylethyl OPQ, and (11) benzyl OPQ were used as inhibition substances and (12) PQQ was used as control.

Degree of inhibition of these substances for aldose reductase is shown in Table 17.

As can be seen from Table 17, OPQs have stronger inhibition of aldose reductase than PQQ.

TABLE 17

Inhibitory effect of OPQs and PQQ on aldose reductase of kidney

| compounds | $1 \times 10^{-5}$ | $5 \times 10^{-6}$ | $2 \times 10^{-6}$ | $1 \times 10^{-6}$ | $5 \times 10^{-7}$ | $2 \times 10^{-7}$ | $1 \times 10^{-7}$ | $5 \times 10^{-8}$ |
|---|---|---|---|---|---|---|---|---|
| OPQ | | | | | | 62.1 | 51.9 | 39.3 |
| Methyl OPQ | | | | 92.1 | 73.6 | 31.4 | 25.0 | |
| 1-Methylpropyl OPQ | | | | | 61.7 | 45.9 | 32.6 | |
| 2-Methylpropyl OPQ | | | | 63.1 | 44.1 | 30.2 | | |
| 2-Carbamoylethyl OPQ | | 89.1 | 75.7 | 59.6 | 44.7 | | | |
| Hydroxymethyl OPQ | | | 68.2 | 57.9 | 41.1 | 26.7 | | |
| 2-Methylthioethyl OPQ | 83.0 | 81.8 | 54.9 | 42.0 | 24.3 | | | |
| 2-Carboxyethyl OPQ | 58.5 | 55.0 | 49.9 | 48.0 | 22.5 | | | |
| 4-Hydroxybenzyl OPQ | 89.0 | 71.3 | 49.4 | 38.6 | | | | |
| 1-Methylethyl OPQ | | 68.2 | 48.1 | 30.5 | | | | |
| Benzyl OPQ | | 63.3 | 46.4 | 35.7 | | | | |
| PQQ | 64.4 | 42.8 | 17.3 | | | | | |

Example 33

Lens of rabbit was homogenized with 10 mM phosphoric acid buffer (pH 7.0) containing 2 mM dithiothreitol in an amount of two times the volume of the lens and subjected to centrifugation. The supernatant liquid was purified by affinity chromatography, gel filtration and chromatofocusing to obtain electrophoretically homogeneous aldose reductase. Using (1) OPQ, (2) 1-methylpropyl OPQ, (3) 2-methylpropyl OPQ, (4) hydroxymethyl OPQ, and (5) 1-methylethyl OPQ as inhibition substances, degree of inhibition of these substances for aldose reductase of rabbit lens was examined in the same manner in Example 32. Degree of inhibition of these substances for aldose reductase is shown in Table 18.

As can be seen from Table 18, OPQs show stronger inhibition of aldose reductase than PQQ.

TABLE 18

Inhibitory effect of OPQs on aldose reductase of lens

| Compounds | $5 \times 10^{-6}$ | $2 \times 10^{-6}$ | $1 \times 10^{-6}$ | $5 \times 10^{-7}$ | $2 \times 10^{-7}$ | $1 \times 10^{-7}$ | $5 \times 10^{-8}$ |
|---|---|---|---|---|---|---|---|
| OPQ | | | | 63.1 | 54.5 | 43.2 | 31.0 |
| 1-Methylpropyl OPQ | | | 64.7 | 50.8 | 36.4 | 24.0 | |
| 2-Methylpropyl OPQ | | | 69.8 | 57.2 | 34.9 | 27.0 | |
| Hydroxymethyl OPQ | | 60.4 | 50.1 | 31.9 | | | |
| 1-Methylethyl OPQ | 68.4 | 51.9 | 43.3 | 33.0 | | | |

Example 34

Eightyfour male Sprague-Davley rats (supplied from Japan Charles River Co.) of four weeks old and having a body weight of 70–80 g were used and the following experiments were conducted. One group consisted of six rats.

The groups included normal group, 50% galactose administration group, PQQ administration group, and OPQ administration group. Commercially available feeding stuff (manufactured by Japan Clea Co.) was given to the rats of normal group, and rats of 50% galactose administration group, PQQ administration group and OPQ administration group were allowed to freely take powdery feeding stuff comprising a mixture of the above-mentioned commercially available powder feeding stuff and D-galactose for food additive in equal weight.

To the rats of PQQ and OPQ administration groups were intraperitoneally administered PQQ.2Na or OPQ in a dosage of 2 mg, 5 mg, 10 mg and 20 mg per 1 kg of rat once a day simultaneously with starting of galactose feeding and until termination of feeding.

On the 6th day and the 9th day from starting of experiment, eyeball was observed by stereoscopic microscope and judgment on cataract was made according to the following criteria.

A0: No muddiness (normal)
A1: Light white muddiness in the surface portion.
A2: A slight heavy white muddiness in the surface portion.
A3: Heavy white muddiness in the surface portion.
A4: Heavy white muddiness in the surface portion and a slight white muddiness in the core portion.
A5: Heavy white muddiness in the surface portion and the core portion.

The results are shown in Table 19.

Advance of cataract was able to be suppressed by intraperitoneal administration of PQQ, but in case of administration of PQQ.2Na in a dosage of 10 mg and 20 mg/kg rat, reduction in body weight was recognized and in case of administration of PQQ.2Na in a dosage of 20 mg/kg rat, some rats died.

On the other hand, advance of cataract was more effectively suppressed by administration of OPQ than administration of PQQ and besides, no rats died being different from administration of PQQ.

TABLE 19

Anti-cataract effect of intraperitoneally administered PQQ, OPQ

| No | Group | Judgement on the 6th day | | | | | | Judgement on the 9th day | | | | | |
|---|---|---|---|---|---|---|---|---|---|---|---|---|---|
| | | $A_0$ | $A_1$ | $A_2$ | $A_3$ | $A_4$ | $A_5$ | $A_0$ | $A_1$ | $A_2$ | $A_3$ | $A_4$ | $A_5$ |
| 1 | Normal group | 6/6 | | | | | | 6/6 | | | | | |
| 2 | 50% galactose administration group | | | 1/6 | 1/6 | 4/6 | | | | | | 4/6 | 2/6 |
| 3 | PQQ administration group PQQ.2Na | | | | | | | | | | | | |
| | 2 mg/kg rat | | 1/6 | 1/6 | | | | | 2/6 | 2/6 | 2/6 | | |
| | 5 mg/kg rat | | 3/6 | 2/6 | 1/6 | | | | | 1/6 | 3/6 | 2/6 | |
| | 10 mg/kg rat | 1/6 | 4/6 | | 1/6 | | | | | 3/6 | 2/6 | 1/6 | |
| | 20 mg/kg rat | 1/6* | 2/6* | | | | | | | 1/6** | 1/6** | | |
| | | (Three rats died.) | | | | | | (Four rats died.) | | | | | |
| 4 | OPQ administration group OPQ | | | | | | | | | | | | |
| | 2 mg/kg rat | | 3/6 | 2/6 | 1/6 | | | 1/6 | 3/6 | 1/6 | 1/6 | | |
| | 5 mg/kg rat | | 2/6 | 3/6 | 1/6 | | | | 2/6 | 2/6 | 2/6 | | |
| | 10 mg/kg rat | | 3/6 | 2/6 | 1/6 | | | | 2/6 | 3/6 | 1/6 | | |
| | 20 mg/kg rat | | 4/6 | 2/6 | | | | | 2/6 | 4/6 | | | |

*Body weight reduced (average 66 g). Body weight of rats of normal group was about 115 g on the average.
**Body weight did not increase (average 77 g). Body weight of rats of normal group was about 141 g on the average.

Example 35

Thirty six male Sprague-Davley rats (supplied from Japan Charles River Co.) four weeks old and having a body weight of 70–80 g were used and the following experiments were conducted. One group consisted of six rats.

The groups included normal group, 50% galactose administration group, PQQ administration group, and OPQ administration group. Commercially available feeding stuff (manufactured by Japan Clea Co.) was given to the rats of normal group, and rats of 50% galactose administration group, PQQ administration group and OPQ administration group were allowed to freely take powdery feeding stuff comprising a mixture of the above-mentioned commercially available powder feeding stuff and D-galactose for food additive in equal weight.

To the rats of PQQ and OPQ administration groups were orally administered PQQ.2Na or OPQ in a dosage of 10 mg and 20 mg per 1 kg of rat once a day simultaneously with starting of galactose feeding and until termination of feeding.

On the 6th day and the 9th day from starting of experiment, eyeball was observed by stereoscopic microscope and judgment on cataract was made according to the same criteria as in Example 34.

The results are shown in Table 20.

Cataract inhibiting effect by oral administration of PQQ was low while advance of cataract was clearly inhibited by oral administration of OPQ.

TABLE 20

Anti-cataract effect of oral administration of OPQ, PQQ

| No | Group | Judgement on the 6th day | | | | | | Judgement on the 9th day | | | | | |
|---|---|---|---|---|---|---|---|---|---|---|---|---|---|
| | | $A_0$ | $A_1$ | $A_2$ | $A_3$ | $A_4$ | $A_5$ | $A_0$ | $A_1$ | $A_2$ | $A_3$ | $A_4$ | $A_5$ |
| 1 | Normal group | 6/6 | | | | | | 6/6 | | | | | |
| 2 | 50% galactose administration group | | | 1/6 | 1/6 | 4/6 | | | | | | 4/6 | 2/6 |
| 3 | PQQ administration group PQQ.2Na | | | | | | | | | | | | |
| | 10 mg/kg rat | | 2/6 | 2/6 | 2/6 | | | | | | 2/6 | 2/6 | 2/6 |
| | 20 mg/ka rat | | 2/6 | 2/6 | 2/6 | | | | | | 2/6 | 3/6 | 1/6 |
| 4 | OPQ administration group OPQ | | | | | | | | | | | | |
| | 10 mg/kg rat | | | 3/6 | 3/6 | | | | | | 2/6 | 4/6 | |
| | 20 mg/kg rat | | 2/6 | 4/6 | | | | | | 3/6 | 3/6 | | |

Example 36

Test on macrophage-chemotaxis (1):

Thirtytwo C3H/He mice (male, 7 weeks old, average body weight 20 g, supplied by Japan Charles River Co.) were divided into 4 groups (A–D) of 8 mice each.

A solution of OPQ in physiological saline of pH 7.0 was intraperitoneally administered to each mouse 7 times, namely, on the 1st day, 2nd day, 3rd day, 4th day, 5th day, 6th day and 7th day. Dosage for one administration per one mouse was as follows: That is, 0.2 ml of the solution containing 0.2 mg/ml of OPQ for group B, 0.2 ml of the solution containing 0.5 mg/ml of OPQ for group C, 0.2 ml of the solution containing 1.0 mg/ml of OPQ for group D and 0.2 ml of physiological saline for group A.

On the 8th day from starting of the experiment, the mice were anesthetized with ether and blood was drawn from carotid artery and 5 ml of cold Hanks solution was intraperitoneally injected and exudate cells for the abdominal cavity were collected. Exudate cells for the abdominal cavity of respective groups were gathered, washed three times with cold Hanks solution and suspended in RPMI medium at $5 \times 10^5$ cells/ml and macrophage-chemotaxis was measured. 50% zymosan treated serum was used as chemotaxis factor and examination was conducted at three points for each sample. Number of chemotaxied macrophage was measured on microscope and 13 visual fields was examined for one point and the results are shown in Table 2. The value in the table is a total number of chemotaxied macrophages at 3 points for each sample.

Preparation of Hanks solution and RPMI medium will be explained below.

| Hanks solution | |
|---|---|
| Hanks solution (Nissui Seiyaku Co.) | 475 ml |
| Lactalbumin | 25 ml |
| 7.5% NAHCO | 1.25 ml |

Respective liquids were sterilized at 121° C. 10 for 15 minutes and aseptically mixed before use.

| RPMI medium | |
|---|---|
| RPMI [Gibco Diagnostics Laboratories (USA)] | 261 ml |
| Fetal Bovine Serum [Flow Laboratories (USA)] | 30 ml |
| $5 \times 10^{-3}$M 2-mercapto ethanol solution | 3 ml |
| Mixture of streptomycin (100 μg/ml) and penicillin G (100 unit/ml) | 3 ml |
| 200 mM L-glutamine solution | 3 ml |

The above components other than Fetal Bovine Serum were filtered and these were aseptically mixed before use.

TABLE 21

| Group | Dosage of OPQ (mg/kg mouse × day) | (1) Chemotaxis factor was not present | (2) Chemotaxis factor was present | (2) − (1) Chemotaxied macrophage | Relative activity of group (%) |
|---|---|---|---|---|---|
| A | No administration | 10 | 68 | 58 | 100 |
| B | 2 mg × 7 days | 11 | 107 | 96 | 166 |
| C | 5 mg × 7 days | 9 | 96 | 87 | 150 |
| D | 10 mg × 7 days | 7 | 180 | 173 | 298 |

Example 37

Test on macrophage-chemotaxis (2):

Test on macrophage-chemotaxis was conducted in the same manner as in Example 36 except that hydroxymethyl OPQ was intraperitoneally administered to each mouce 3 times of the 1st day, the 2nd day and the 3rd day in the following dosage for one administration per one mouse: 0.2 ml of hydroxymethyl OPQ solution containing 0.5 mg/ml of hydroxymethyl OPQ for group B, 0.2 ml of the solution containing 1.0 mg/ml of hydroxymethyl OPQ for group C, and 0.2 ml of the solution containing 1.5 mg/ml of hydroxymethyl OPQ for group D and exudate cells for the abdominal cavity were collected on the 4th day from starting of experiment. The results are shown in Table 22.

TABLE 22

| Group | Dosage of hydroxymethyl OPQ (mg/kg mouse × day) | (1) Chemotaxis factor was not present | (2) Chemotaxis factor was present | (2) − (1) Chemotaxied macrophage | Relative activity of group (%) |
|---|---|---|---|---|---|
| A | No administration | 11 | 40 | 29 | 100 |
| B | 5 mg × 3 days | 17 | 61 | 44 | 152 |
| C | 10 mg × 3 days | 10 | 66 | 56 | 193 |
| D | 15 mg × 3 days | 9 | 48 | 39 | 134 |

Example 38

Test on T cell blast transformation reaction (1):

In the same manner as in Example 36, OPQ was administered to C3H/He mouse and the mouse was bred. Dosage of OPQ for one administration per one mouse was 0.2 ml of OPQ solution containing 0.5 mg/ml of OPQ for group B and 0.2 ml of the solution containing 1.0 mg/ml of OPQ for group C and 0.2 ml of physiological saline was administered for group A.

On the 8th day from starting of experiment, mouse was anesthetized with ether and blood was drawn from carotid artery and spleen was aseptically extracted.

Cells of the spleen of respective groups were broken up and these cells were floated on tris-NH$_4$Cl hemolytic solution warmed to 37° C. and left for 5 minutes at 37° C. to hemolyze erythrocytes, followed by washing twice with cold Hanks solution. The cells were suspended in RPMI medium at $4 \times 10^6$ cells/ml and the suspension was put in a flat bottom microplate of 96 holes. Culture was carried out in the air containing 5% of CO$_2$ at 37° C. using concanavalin A (Type IV Sigma C2010) in an amount of 0.5 μg/ml or 2 μg/ml as mitogen. After 63 hours from starting of culture, $^3$H-thymidine was added in an amount of 2.5 μci/ml and culturing was carried out for further 9 hours. Thereafter, cells were gathered on a glass fiber filter by cell harvester and $^3$H on this filter was measured by a liquid scintillation counter.

As control, same four culturings were conducted under the same conditions without adding concanavalin A.

The results are shown in Table 23. Values in the table are average values of intake amount (cpm) of $^3$H in culture under four same conditions.

The tris-NH$_4$Cl hemolytic solution was prepared in the following manner.

| Trim-NH4Cl hemolytic solution: | |
|---|---|
| 0.16M NH4Cl | 90 ml |
| 0.17M tris (adjusted to pH 7.65 with HCl) | 10 ml |

The above two liquids were mixed and the mixture was adjusted to pH 7.2 and sterilized at 121° C. for 15 minutes.

TABLE 23

| Group | Dosage of OPQ (mg/kg mouse × day) | Concentration of concanavalin (μg/ml) 0 | 0.5 | 2 | Relative activity (%) Concanavalin A 0.5 μg/ml | 2.0 μg/ml |
|---|---|---|---|---|---|---|
| A | No administration | 7312 (cpm) | 11637 (cpm) | 96188 (cpm) | 100 | 100 |
| B | 5 mg × 7 days | 10796 | 15942 | 140376 | 137 | 146 |
| C | 10 mg × 7 days | 9124 | 21965 | 144171 | 189 | 150 |

Example 39

Test on T cell blast transformation reaction (2):

Cells of spleen were obtained in the same manner as in Example 38 except that OPQ was not administered using five C3H/He mice (male, 7 weeks old, average body weight of 20 g, supplied by Japan Charles River Co.).

Then, the cells were suspended in RPMI medium at $4 \times 10^6$ cells/ml and the suspension was put in a flat bottom microplate of 96 holes. Culture was carried out in the air containing 5% of $CO_2$ at 37° C. using 1.0 μg/ml of concanavalin A as mitogen with addition of 0.5 or 2.0 μg/ml of OPQ. After 63 hours from starting of culture, $^3$H-thymidine was added at 2.5 μCi/ml and culture was carried out for further 9 hours. Thereafter, cells were gathered on a glass fiber filter by cell harvester and $^3$H on the filter was measured by a liquid scintillation counter.

As control, same four cultures were conducted under respective conditions without adding concanavalin A or OPQ. The results are shown in Table 24. Values in the table are average values of intake amount (cpm) of $^3$H in culture under four same conditions. Activity acceleration effect of OPQ was not recognized when concanavalin A was not added, but activity acceleration effect of OPQ was recognized when concanavalin A was added.

TABLE 24

| Dosage of OPQ (μg/ml) | Concentration of concanavalin (μg/ml) 0 | 1.0 | Relative actitity (%) Concanavalin A 1.0 μg/ml |
|---|---|---|---|
| 0 | 2077 (cpm) | 89091 (cpm) | 100 |
| 0.5 | 1946 | 130775 | 146 |
| 2.0 | 2031 | 116093 | 130 |

Example 40

Test on B cell blast transformation reaction:

Cells of spleen of C3H/He mice to which OPQ was administered were obtained in the same manner as in Example 38.

Further, intake amount of $^3$H-thymidine was examined in the same manner as in Example 38 except that 25 μg/ml or 50 μg/ml of lipopolysaccharide (LPS WE *E. coli* 0111, Difco) was used in place of the concanavalin A as mitogen. The results are shown in Table 25. Values in the table are average values of intake amount (cpm) of $^3$H in culture under four same conditions.

TABLE 25

| Group | Dosage of OPQ (mg/kg mouse × day) | Concentration of Lipopolysaccharide (LPS) (μg/ml) 0 | 25 | 50 | Relative activity (%) Lipopolysaccharide 25 μg/ml | 50 μg/ml |
|---|---|---|---|---|---|---|
| A | No administration | 6562 (cpm) | 34557 (cpm) | 42247 (cpm) | 100 | 100 |
| B | 5 mg × 7 days | 9303 | 37434 | 46193 | 108 | 109 |
| C | 10 mg × 7 days | 9301 | 41876 | 53267 | 121 | 126 |

In Examples 36–40, macrophage activity was examined according to chemotaxis of peritoneal macrophage (literature 1) and activity of T cell and that of B cell were examined according to blast transformation reaction using concanavalin A and lipopolysaccharide, (LPS) as mitogen (literature 2).

Literature 1: "Function of Macrophage and Method of Measurement of Function", pages 61–65 1985), edited by Educational Committee of Japan Bacteriological Society and published from Saikon Shuppan Co.)

Literature 2: "New Method of Searching of Function of Lymphocytes", pages 350–355 (1987) edited by Junichi Yada and Michio Fujiwara and published from Chugai Igaku Co.

Example 41

Pharmacological activity (1) of OPQs on carbon tetrachloride ($CCl_4$)-induced liver diseases:

Twentyfive SD rats (male, 7 weeks old, body weight: about 220 g; supplied by Japan Charles River Co.) were divided to five groups (A-E) each consisting of five rats.

All rats were fasted for 16 hours and 1.1 ml of solutions containing 0.4 mg/ml, 1.0 mg/ml and 2.0 mg/ml of OPQ were intraperitoneally administered to the rats of groups C, D and E, respectively and furthermore, after 40 minutes, OPQ in the same dosage as above was intraperitoneally administered, respectively. In these cases, OPQ was used as a solution in physiological saline. To the rats of group B was intraperitoneally administered 1.1 ml of physiological saline in place of the OPQ solution.

Furthermore, after 20 minutes, 2.2 ml of 10% carbon tetrachloride solution (in olive oil) was administered to stomach of the rats of groups B-E. Neither OPQ nor carbon tetrachloride was administered to the rats of group A.

After 24 hours from administration of carbon tetrachloride, blood was collected from abdominal aorta and serum was obtained by centrifugal separation.

GPT, GOT and amount of total bilirubin were measured by clinical examination reagent (trademark: FUJI Dry Chemslide manufactured by Fuji Photo Film Co., Ltd.). The results are shown in Table 26 by average value of five rats.

GPT, GOT and amount of total bilirubin which increased by administration of carbon tetrachloride all markedly decreased by administration of OPQ and it can be seen that OPQ has inhibitory effect on liver diseases.

TABLE 26

| Group | Administration of compound | Administration of CCl₄ | GPT (U/l) | GOT (U/l) | Total bilirubin (mg/dl) |
|---|---|---|---|---|---|
| A | No administration | No administration | 24 | 140 | 0.9 |
| B | No administration | 1 ml/kg rat | 1521 | 3266 | 1.5 |
| C | OPQ 2 mg/kg rat twice | 1 ml/kg rat | 1057 | 2402 | 1.2 |
| D | OPQ 5 mg/kg rat twice | 1 ml/kg rat | 553 | 1892 | 1.2 |
| E | OPQ 10 mg/kg rat twice | 1 ml/kg rat | 650 | 1907 | 1.1 |

Example 42

Pharmacological activity (2) of OPQs on carbon tetrachloride (CCl₄)-induced liver diseases:

Pharmacological activity of OPQs for carbon tetrachloride-induced liver diseases was examined in the same manner as in Example 41 except that 1-methylpropyl OPQ, 2-methylthioethyl OPQ and benzyl OPQ were respectively administered twice in a dose of 5 mg/kg rat in place of the OPQ. The results are shown in Table 27.

GPT, GOT and total amount of bilirubin which increased by administration of carbon tetrachloride sharply decreased by administration of 1-methylpropyl OPQ, 2-methylthioethyl OPQ or benzyl OPQ. It can be seen that OPQs have inhibitory effect on liver diseases.

TABLE 27

| Group | Administration of compound | Administration of CCl₄ | GPT (U/l) | GOT (U/l) | Total bilirubin (mg/dl) |
|---|---|---|---|---|---|
| A | No administration | No administration | 16 | 144 | 0.5 |
| B | No administration | 1 ml/kg rat | 818 | 3308 | 1.2 |
| C | 1-Methylpropyl OPQ 5 mg/kg rat twice | 1 ml/kg rat | 182 | 887 | 0.7 |
| D | 2-Methlthioethyl OPQ 5 mg/kg rat twice | 1 ml/kg rat | 157 | 693 | 0.7 |
| E | Benzyl OPQ 5 mg/kg rat twicet | 1 ml/kg rat | 233 | 993 | 0.7 |

Example 43

Pharmacological effect of OPQ on D-galactosamine-induced liver diseases:

Thirty SD rats (male, 7 weeks old, body weight: about 240 g; supplied by Japan Charles River Co.) were divided to six groups (A-F) each consisting of five rats. All rats were fasted for 18 hours and 1.2 ml of solutions containing 0.4 mg/ml, 1.0 mg/ml, 2.0 mg/ml, and 3.0 mg/ml of OPQ were intraperitoneally administered to rats of groups C, D, E and F, respectively, and furthermore, after lapse of 40 minutes, OPQ in the same doses as above were intraperitoneally administered to the rats, respectively. In these cases, the OPQ was dissolved in physiological saline and administered to the rats. For the rats of group B, 1.2 ml of physiological saline was intraperitoneally administered in place of the OPQ solution.

Furthermore, after lapse of 20 minutes, 1.2 ml of a solution containing 0.2 mg/ml of D-galactosamine was subcutaneously injected to the rats of groups B-F. Neither OPQ nor D-galactosamine was administered to the rats of group A.

After lapse of 23 hours from administration of D-galactosamine, blood was collected from abdominal aorta and serum was obtained by centrifugal separation.

GPT, GOT and total amount of bilirubin were measured by clinical examination reagent (trademark: FUJI DRYCHEMSLIDE manufactured by Fuji Photo Film Co., Ltd.). The results are shown in Table 28 by average value of five rats.

GPT, GOT and total amount of bilirubin which increased by administration of D-galactosamine all sharply decreased by administration of OPQ and it can be seen that OPQ has inhibitory effect on liver diseases.

TABLE 28

| Group | Administration of compound | Administration of D-galactosamine | GPT (U/l) | GOT (U/l) | Total bilirubin (mg/dl) |
|---|---|---|---|---|---|
| A | No administration | No administration | 20 | 214 | 0.8 |
| B | No administration | 1 g/kg rat | 328 | 868 | 0.9 |
| C | OPQ 2 mg/kg rat twice | 1 g/kg rat | 266 | 729 | 0.8 |
| D | OPQ 5 mg/kg rat twice | 1 g/kg rat | 178 | 529 | 0.6 |
| E | OPQ 10 mg/kg rat twice | 1 g/kg rat | 162 | 552 | 0.6 |
| F | OPQ 15 mg/kg rat twice | 1 g/kg rat | 160 | 652 | 0.6 |

We claim:

1. A process for producing oxazopyrroloquinolines represented by the following formula [I]:

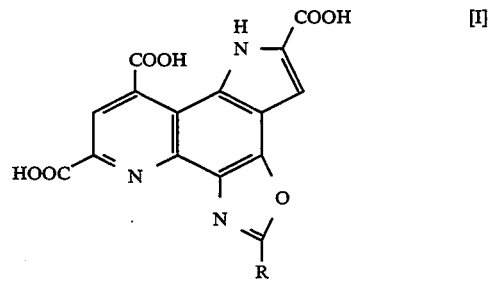

wherein R represents hydrogen or a lower alkyl group having 1 to 4 carbon atoms which may be substituted by a substituent selected from the group consisting of hydroxyl, carboxy, mercapto, amino, carbamoyl, phenyl, hydroxyphenyl, guanidino, imidazolyl and methylmercapto groups which process comprises culturing microorganisms capable of producing pyrroloquinolinequinone in a medium using methanol as a carbon source and are those which belong to Genus Methylobacillus, Genus Methylophilus, Genus Methylobacterium, Genus Ancylobacter, Genus Hyphomicrobium, Genus Xanthobacter, Genus Acidomonus, Genus Paracoccus, Genus Thiobacillus, Genus Methylophage, or Genus Mycobacterium to obtain a culture broth containing pyrroloquinolinequinone, adding to the culture broth at least one compound selected from the group consisting of amino acids and monomethylamine in the presence of oxygen to convert pyrroloquinolinequinone in the culture broth to oxazopyrroloquinoline and recovering the oxazopyrroloquinoline from the culture broth.

2. A process according to claim 1, wherein amount of the α-amino acids or monomethylamine is not less than 1 mot based on 1 mol of pyrroloquinolinequinone contained in the culture broth.

3. A process according to claim 1, wherein temperature of reaction solution is 20°–100° C.

* * * * *